(12) United States Patent
Ravichandran et al.

(10) Patent No.: US 6,677,392 B2
(45) Date of Patent: Jan. 13, 2004

(54) PHOTOSTABLE, SILYLATED BENZOTRIAZOLE UV ABSORBERS AND COMPOSITIONS STABILIZED THEREWITH

(75) Inventors: Ramanathan Ravichandran, Suffern, NY (US); Joseph Suhadolnik, Yorktown Heights, NY (US); Mervin G. Wood, Poughquag, NY (US); Rong Xiong, Dobbs Ferry, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 45 days.

(21) Appl. No.: 09/919,974

(22) Filed: Aug. 1, 2001

(65) Prior Publication Data

US 2002/0115753 A1 Aug. 22, 2002

Related U.S. Application Data

(60) Provisional application No. 60/222,783, filed on Aug. 3, 2000, and provisional application No. 60/303,048, filed on Jul. 5, 2001.

(51) Int. Cl.$^7$ ................................................. C08K 5/45
(52) U.S. Cl. .................... 524/86; 548/100; 548/255; 548/257; 548/260; 524/91; 524/104; 524/106; 524/167; 524/261; 524/543; 524/567; 524/570
(58) Field of Search .......................... 548/100, 255, 548/257, 260; 524/86, 91, 104, 106, 167, 261, 543, 567, 570

(56) References Cited

U.S. PATENT DOCUMENTS

| | | | |
|---|---|---|---|
| 4,322,455 A | 3/1982 | Olson et al. | 427/160 |
| 4,373,060 A * | 2/1983 | Ching | 524/767 |
| 4,373,061 A | 2/1983 | Ching | 524/767 |
| 4,439,494 A | 3/1984 | Olson | 428/412 |
| 4,859,759 A | 8/1989 | Maycock et al. | 528/27 |
| 5,185,445 A | 2/1993 | Meuwly et al. | 544/216 |
| 5,219,905 A | 6/1993 | Carrozza et al. | 524/102 |
| 5,321,066 A | 6/1994 | Carrozza et al. | 524/103 |
| 5,391,795 A | 2/1995 | Pickett | 556/436 |
| 5,418,267 A | 5/1995 | Carrozza et al. | 524/99 |
| 5,463,058 A | 10/1995 | Carrozza et al. | 546/14 |
| 5,578,665 A | 11/1996 | Carrozza et al. | 524/99 |
| 5,679,820 A | 10/1997 | Pickett et al. | 556/436 |
| 5,707,690 A | 1/1998 | Valet et al. | 427/402 |
| 5,756,793 A | 5/1998 | Valet et al. | 556/436 |
| 5,837,792 A | 11/1998 | Meuwly et al. | 528/27 |
| 6,005,036 A | 12/1999 | Carrozza et al. | 524/265 |
| 6,166,218 A | 12/2000 | Ravichandran et al. | 548/257 |

FOREIGN PATENT DOCUMENTS

| EP | 0732361 | 9/1996 |
|---|---|---|
| EP | 0732361 A1 * | 9/1996 |
| EP | 0675108 | 6/1998 |

\* cited by examiner

Primary Examiner—D. R. Wilson
Assistant Examiner—William K Cheung
(74) Attorney, Agent, or Firm—Tyler A. Stevenson

(57) ABSTRACT

Photostable, silylated benzotriazole compounds of formula (I) or (II)

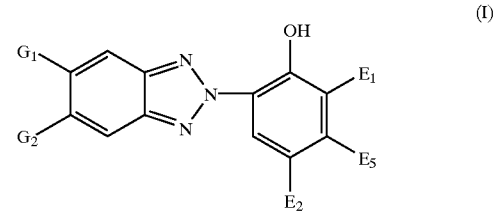

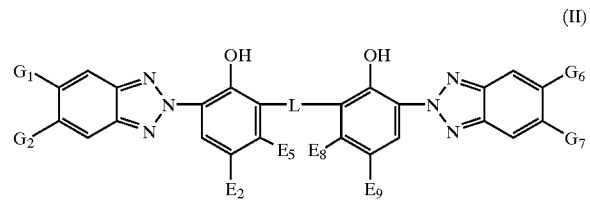

where at least one of $E_1$, $E_2$, $E_5$, $E_8$, $E_9$, $G_2$ and $G_7$ is a silylated group; and $G_2$ and/or $G_7$ is an electron withdrawing moiety or $E_1$ is α-cumyl, are both photostable and particularly compatible in high performance coatings such as organopolysiloxanes.

23 Claims, No Drawings

PHOTOSTABLE, SILYLATED BENZOTRIAZOLE UV ABSORBERS AND COMPOSITIONS STABILIZED THEREWITH

This application claims the benefit under 35 USC 119(e) of U.S. Provisional Application Serial Nos. 60/222,783, filed Aug. 3, 2000 and 60/303,048, filed Jul. 5, 2001.

The instant invention pertains to photostable, silylated benzotriazole UV absorbers and compositions stabilized therewith. These benzotriazole compounds are novel and exhibit enhanced durability due to either the incorporation of electron withdrawing moieties at the 5-position of the benzo ring or to the presence of an α-cumyl group on the phenol ring. The polymer compositions containing said benzotriazoles are advantageously stabilized, especially high performance coatings such as organopolysiloxanes. The instant compounds are red-shifted and show increased absorption in the 350–400 nm region of the UV spectrum.

BACKGROUND OF THE INVENTION

Copending patent application Ser. No. 08/981,433, now U.S. Pat. No. 6,005,036, describes polysiloxanes themselves which are useful as process stabilizers.

U.S. Pat. No. 4,859,759 describes in the most generic manner siloxane compounds containing at least one benzotriazole and one hindered amine substituent covalently coupled to a silicon atom. This reference does not supply any specific exemplification of such structures. The particular structures of the instant invention are neither disclosed nor suggested by this reference.

U.S. Pat. Nos. 5,707,690 and 5,756,793 disclose the use of silylated benzophenones for the protective coatings for wood. EP 675,108 B1 describes thioether substituted benzophenone UV absorbers which may also contain silylated substituents.

U.S. Pat. Nos. 5,185,445 and 5,837,792 describe polysiloxane light stabilizers which contain pendant hydroxyphenyl-diaryl-s-triazine moieties.

U.S. Pat. Nos. 5,219,905; 5,321,066; 5,418,267; 5,463,058 and 5,578,665 disclose hindered amines containing siloxane and other silyl moieties as stabilizers.

U.S. Pat. Nos. 5,391,795 and 5,679,820 describe the preparation and use of silylated benzophenone UV absorbers. U.S. Pat. No. 5,391,795 compares these silylated benzophenone UV absorbers with one example of a silylated benzotriazole UV absorber which is 2-{2-hydroxy-5-[3-(3-triethoxysilyl)propylcarbamoyloxy]propylphenyl}2H-benzotriazole. This silylated benzotriazole compound contains neither a bulky substituent ortho to the hydroxy group in the phenyl ring nor an electron withdrawing group at the 5-position of the benzo ring. Both of these two substitution patterns are shown to be particularly efficacious in enhancing long term photostability of the benzotriazoles. The electron withdrawing group at the 5-position of the benzo ring allows for the red-shifting of the UV spectrum of the benzotriazoles.

U.S. Pat. No. 4,373,061 teaches the use of silicone coatings for unprimed plastic substrates and coated articles. The silicone coating contains a UV absorbing organic group attached to silicon by carbon-silicon bonds. The UV absorber is a silylated hydroxy-benzophenone.

U.S. Pat. No. 4,322,455 describes a process for producing an ultraviolet radiation stabilized polymeric article which contains on the surface of said article a UV absorbing composition. The UV absorber may be generically any of the known types of compounds such as benzophenones, benzotriazole, cyanoacrylates or benzylidene malonates. The only benzotriazole disclosed is 2-(2-hydroxy-5-tert-octylphenyl)-2H-benzotriazole.

Copending application Ser. No. 09/234,880, now U.S. Pat. No. 6,166,218, demonstrates the value of having such substitution at the 3-position of the phenyl ring by a bulky group and at the 5-position of the benzo ring by an electron withdrawing moiety. All the instant compounds have an electron withdrawing moiety at the 5-position of the benzo ring. When there is a bulky substituent at the 3-position of the phenyl ring, particularly an α-cumyl group, the photostability of the benzotriazole is particularly enhanced.

OBJECTS OF THE INVENTION

The first object of this invention is to provide for new monomeric benzotriazole UV absorbers which contain silicon moieties.

Another object of this invention is to provide silicone/siloxane hardcoat or softcoat resin compositions containing said benzotriazole UV absorbers which can be added to or copolymerized into such hardcoat or softcoat resins.

Still another object of the invention is to provide for articles which contain the siliconelsiloxane hardcoat or softcoat composition as a screening layer in a laminate composition, such as over polycarbonate.

Another object of the invention is provide automotive coating compositions which the instant compounds are melamine/siloxane crosslinked structures.

Still another object of the invention is to provide for polymer compositions where the instant compounds are used in conjunction with silylated hindered amines including inter alia N-hydrocarbyloxy and N-hydroxyalkyloxy substituted hindered amines.

Still another object of the invention is to provide for silicone/siloxane hardcoat or softcoat compositions containing post-added other advanced benzotriazoles which do not contain silicon moieties and with or without the concomitant presence of hindered amines, N-hydrocarbyloxy- or N-hydroxyalkyloxy-substituted hindered amines.

DETAILED DISCLOSURE

The instant invention pertains to benzotriazole compounds of formula (I) or (II)

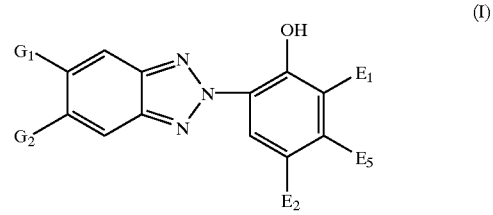

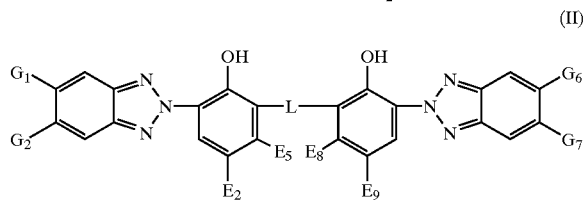

wherein $G_1$ and $G_6$ are independently hydrogen or halogen;

$G_2$ and $G_7$ are independently cyano, perfluoroalkyl of 1 to 12 carbon atoms, fluoro, chloro, —CO—$G_3$, —COOG$_3$, —CONHG$_3$, —CON(G$_3$)$_2$, E$_3$SO—, E$_3$SO$_2$—, —PO(C$_6$H$_5$)$_2$,

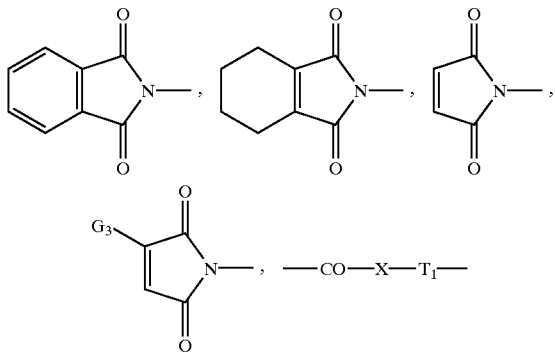

O—CO—NH—T$_2$—Si(OR$_2$)$_n$(R$_1$)$_{3-n}$ or —CO—X—T$_1$—Si(OR$_2$)$_n$(R$_1$)$_{3-n}$;

or G$_7$ is also hydrogen;

or G$_2$ may also be hydrogen when E$_1$ is a group of formula (IV) or (V);

T$_1$ and T$_2$ are independently alkylene of 1 to 18 carbon atoms, preferably alkylene of 2 or 3 carbon atoms, or alkylene-phenylene-alkylene of 8 to 20 carbon atoms;

R$_1$ and R$_2$ are independently alkyl of 1 to 18 carbon atoms, cycloalkyl of 5 to 12 carbon atoms, aryl of 6 to 10 carbon atoms or phenylalkyl of 7 to 20 carbon atoms, preferably alkyl of 1 to 6 carbon atoms or phenyl;

n is 0, 1, 2 or 3;

X is —O—, —NE$_4$— or —NH—;

G$_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;

E$_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms or by one or more of the following groups —T$_1$—Si(OR$_2$)$_n$(R$_1$)$_{3-n}$, —T$_1$—X—CO—X—T$_2$—Si(OR$_2$)$_n$(R$_1$)$_{3-n}$, —T$_1$—CO—X—T$_2$—Si(OR$_2$)$_n$(R$_1$)$_{3-n}$, —X—T$_1$—Si(OR$_2$)$_n$(R$_1$)$_{3-n}$, or —X—T$_1$—X—CO—X—T$_2$—Si(OR$_2$)$_n$(R$_1$)$_{3-n}$;

or E$_1$ is alkyl of 1 to 24 carbon atoms substituted by one or two hydroxy groups;

or E$_1$ is a group of formula (IV) or (V)

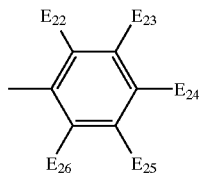

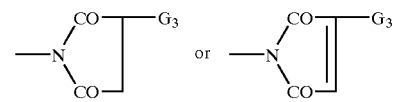

where

E$_{27}$ and E$_{28}$ are independently alkyl of 1 to 18 carbon atoms, or cycloalkyl of 5 to 12 carbon atoms;

E$_{22}$, E$_{23}$, E$_{24}$, E$_{25}$ and E$_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOE$_{11}$, —OE$_4$, —NCO, —NHCOE$_{11}$, or —NE$_7$E$_8$, or mixtures thereof, where E$_4$ is straight or branched chain alkyl of 1 to 24 carbon atoms or straight or branched alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof; or E$_{22}$, E$_{23}$, E$_{24}$, E$_{25}$ and E$_{26}$ are independently phenyl, —OH, —OCOE$_{11}$, —OE$_{29}$, —NCO, —NHCOE$_{11}$, or —NE$_7$E$_8$, cyano, nitro, perfluoroalkyl of 1 to 12 carbon atoms, —COG$_3$, —COOG$_3$, —CON(G$_3$)$_2$, —CONHG$_3$, E$_3$S—, E$_3$SO—, E$_3$SO$_2$—, —P(O)(C$_6$H$_5$)$_2$, —P(O))OG$_3$)$_2$, —SO$_2$—X$_1$—E$_{29}$;

X$_1$ is —O—, —NH— or —NE$_4$—;

E$_{29}$ is straight or branched chain alkyl of 1 to 24 carbon atoms, straight or branched chain alkenyl of 2 to 18 carbon atoms, said alkyl or said alkenyl substituted by one or more —OH, —OCOE$_{11}$, —OE$_4$, —NCO, —NHCOE$_{11}$, —NE$_7$E$_8$, phthalimido,

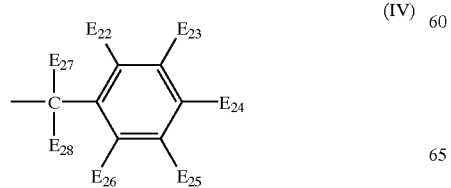

or mixtures thereof, where E$_4$ is straight or branched chain alkyl of 1 to 24 carbon atoms or alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof; or E$_{29}$ is phenyl or phenylalkyl of 7 to 15 carbon atoms, or said phenyl or said phenylalkyl substituted by one to three alkyl groups of 1 to 4 carbon atoms;

E$_2$ and E$_9$ are independently hydrogen, straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms or by one or more of the following groups —T$_1$—Si(OR$_2$)$_n$(R$_1$)$_{3-n}$, —T$_1$—X—CO—X—T$_2$—Si(OR$_2$)$_n$(R$_1$)$_{3-n}$, —T$_1$—CO—X—T$_2$—Si(OR$_2$)$_n$(R$_1$)$_{3-n}$, —X—T$_1$—Si(OR$_2$)$_n$(R$_1$)$_{3-n}$ or —X—T$_1$—X—CO—X—T$_2$—Si(OR$_2$)$_n$(R$_1$)$_{3-n}$; or E$_2$ and E$_9$ are independently said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where E$_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof; or E$_1$, E$_2$ and E$_9$ are also independently —T$_1$—Si(OR$_2$)$_n$(R$_1$)$_{3-n}$, —T$_1$—X—CO—X—T$_2$—Si(OR$_2$)$_n$(R$_1$)$_{3-n}$ or —T$_1$—CO—X—T$_2$—Si(OR$_2$)$_n$(R$_1$)$_{3-n}$;

E$_{11}$ is hydrogen, straight or branched chain alkyl of 1 to 18 carbon atoms, straight or branched chain alkenyl of 2 to 18 carbon atoms, cycloalkyl of 5 to 12 carbon atoms, aryl of 6 to 14 carbon atoms or phenylalkyl of 7 to 15 carbon atoms;

L is alkylene of 1 to 12 carbon atoms, alkylidene of 2 to 12 carbon atoms, benzylidene, p-xylylene, cycloalkylidene of 5 to 12 carbon atoms or α,α,α',α'-tetramethyl-m-xylylene;

E$_3$ is alkyl of 1 to 20 carbon atoms, said alkyl substituted by alkoxycarbonyl of 2 to 9 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, E$_5$ and E$_8$ are independently the same as E$_2$; or E$_5$ and E$_8$ are independently hydrogen, —X—E$_1$, —X—CO—E$_2$, —X—CO—X$_1$, —X—T$_1$—Si(OR$_2$)$_n$(R$_1$)$_{3-n}$ or —X—T$_1$—X—CO—X—T$_2$—Si(OR$_2$)$_n$(R$_1$)$_{3-n}$;

X$_1$ is —NH—E$_4$ or —X—E$_2$;

with the proviso that at least one of G$_2$, G$_7$, E$_1$, E$_2$, E$_5$, E$_8$ and E$_9$ contains a group —T$_1$—Si(OR$_2$)$_n$(R$_1$)$_{3-n}$, —T$_1$—X—CO—X—T$_2$—Si(OR$_2$)$_n$(R$_1$)$_{3-n}$, —T$_1$—CO—X—T$_2$—Si(OR$_2$)$_n$(R$_1$)$_{3-n}$, —X—T$_1$—Si(OR$_2$)$_n$(R$_1$)$_{3-n}$ or —X—T$_1$—X—CO—X—T$_2$—Si(OR$_2$)$_n$(R$_1$)$_{3-n}$; where T$_1$ and T$_2$ are independently alkylene of 1 to 18 carbon atoms or alkylene-phenylene-alkylene of 8 to 20 carbon atoms, and R$_1$ and R$_2$ are independently alkyl of 1 to 18 carbon atoms, cycloalkyl of 5 to 12 carbon atoms, aryl of 6 to 10 carbon atoms or phenylalkyl of 7 to 20 carbon atoms, preferably alkyl of 1 to 3 carbon atoms or phenyl, and n is 0, 1, 2 or 3.

Preferably, the new benzotriazole is a compound of formula IA or IIA

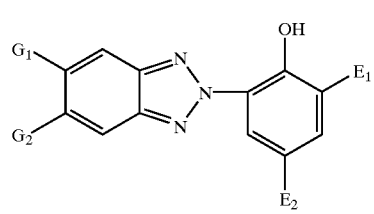

(IA)

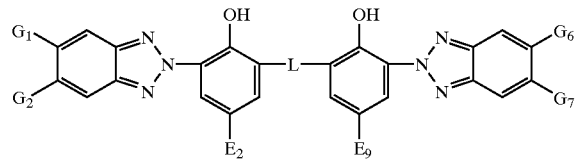

(IIA)

wherein
G$_1$ and G$_6$ are hydrogen,
G$_2$ and G$_7$ are independently cyano, CF$_3$—, fluoro, —CO—G$_3$ or E$_3$SO$_2$—, or G$_7$ is also hydrogen,
G$_3$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms,
E$_1$ is phenylalkyl of 7 to 15 carbon atoms, phenyl, or said phenyl or said phenylalkyl substituted on the phenyl ring by 1 to 4 alkyl of 1 to 4 carbon atoms,
E$_2$ and E$_9$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or E$_2$ is said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where E$_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof;

E$_{11}$ is hydrogen, straight or branched chain alkyl of 1 to 18 carbon atoms, straight or branched chain alkenyl of 2 to 18 carbon atoms, cycloalkyl of 5 to 12 carbon atoms, aryl of 6 to 14 carbon atoms or phenylalkyl of 7 to 15 carbon atoms;

E$_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms;

L is methylene; and with the proviso that at least one of E$_1$, E$_2$ and E$_9$ contains a group —T$_1$—Si(OR$_2$)$_n$(R$_1$)$_{3-n}$, —T$_1$—X—CO—X—T$_2$—Si(OR$_2$)$_n$(R$_1$)$_{3-n}$, —T$_1$—CO—X—T$_2$—Si(OR$_2$)$_n$(R$_1$)$_{3-n}$, —X—T$_1$—Si(OR$_2$)$_n$(R$_1$)$_{3-n}$ or —X—T$_1$—X—CO—X—T$_2$—Si(OR$_2$)$_n$(R$_1$)$_{3-n}$;

where T$_1$ and T$_2$ are independently alkylene of 2 or 3 carbon atoms, and R$_1$ and R$_2$ are independently alkyl of 1 to 6 carbon atoms or phenyl, and n is 0, 1, 2 or 3.

nother preferred embodiment of the instant invention is a compound of formula IA

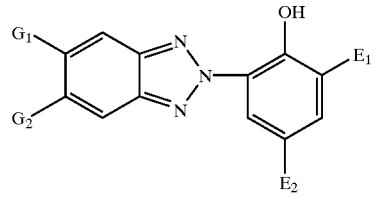

(IA)

wherein
G₁ is hydrogen,
G₂ is CF₃—, fluoro or E₃SO₂—,
E₁ is hydrogen or straight or branched alkyl of 2 to 24 carbon atoms,
E₂ is as defined above, and
E₃ is straight or branched chain alkyl of 1 to 7 carbon atoms,
with the proviso that E₂ contains a group —T₁—Si(OR₂)$_n$(R₁)$_{3-n}$, —T₁—X—CO—X—T₂—Si(OR₂)$_n$(R₁)$_{3-n}$, —T₁—CO—X—T₂—Si(OR₂)$_n$(R₁)$_{3-n}$, —X—T₁—Si(OR₂)$_n$(R₁)$_{3-n}$ or —X—T₁—X—CO—X—T₂—Si(OR₂)$_n$(R₁)$_{3-n}$; where T₁ and T₂ are independently alkylene of 2 or 3 carbon atoms, and R₁ and R₂ are independently alkyl of 1 to 6 carbon atoms or phenyl, and n is 0, 1, 2 or 3.

Preferably, the compound of formula (I) is
(a) 5-trifluoromethyl-2-[2-hydroxy-3-(3-triethoxysilyl)propyl-5-tert-octylphenyl]-2H-benzo-triazole;
(b) 5-trifluoromethyl-2-{2-hydroxy-3-tert-butyl-5-[3-(3-triethyoxysilyl)propylcarbamoyloxy)-propyl]phenyl}2H-benzotriazole;
(c) 5-trifluoromethyl-2-{2-hydroxy-3-tert-butyl-5-[2-(3-triethyoxysilyl)propylcarbamoyl-oxy)ethyl]phenyl}-2H-benzotriazole;
(d) 5-trifluoromethyl-2-{2-hydroxy-5-[2-(3-triethyoxysilyl)propyl-carbamoyloxy)ethyl]-phenyl}-2H-benzotriazole;
(e) 5-trifluoromethyl-2-{2-hydroxy-3-α-cumyl-5-[2-(3-triethyoxysilyl)propylcarbamoyl-oxy)ethyl]phenyl}-2H-benzotriazole;
(f) 5-trifluoromethyl-2-{2-hydroxy-3-tert-butyl-5-[2-(3-(diethoxymethylsilyl)propylamino-carbonylethyl]phenyl}-2H-benzotriazole;
(g) 5-phenylsulfonyl-2-{2-hydroxy-3-tert-butyl-5-[3-(2-ethoxydimethylsilyl)ethylcarbonyl-oxy)propyl]phenyl}-2H-benzotriazole;
(h) 5-n-butylsulfonyl-2-{2-hydroxy-3-tert-butyl-5-[2-(3-ethoxydimethylsilyl)propyl-oxycarbonyl)ethyl]phenyl}-2H-benzotriazole;
(i) 5-trifluoromethyl-2-[2-hydroxy-3-(ethoxydimethylsilyl)propyl-5-tert-octylphenyl]-2H-benzotriazole;
(j) 5-trifluoromethyl-2-[2-hydroxy-3-(trimethylsilyl)propyl-5-tert-butylphenyl]-2H-benzo-triazole;
(k) 5-[3-(diethoxyethylsilyl)propoxycarbonyl]-2-(2-hydroxy-3-α-cumyl-5-tert-octyl-phenyl)-2H-benzotriazole;
(l) 5-[3-(diethoxyethylsilyl)propylaminocarbonyl]-2-(2-hydroxy-3-α-cumyl-5-tert-octyl-phenyl)-2H-benzotriazole;

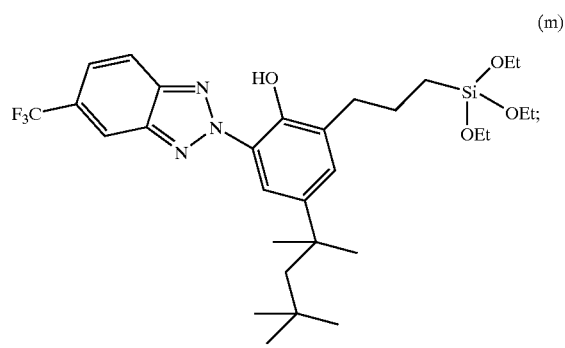

(m)

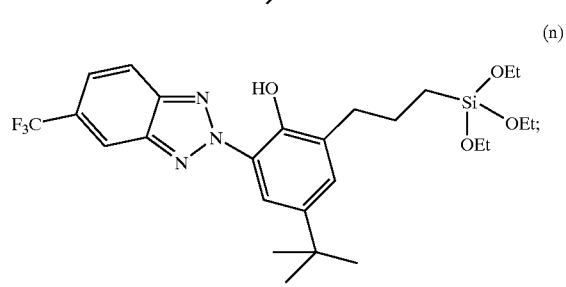

(n)

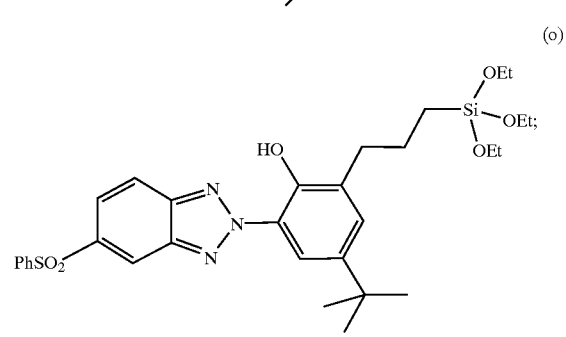

(o)

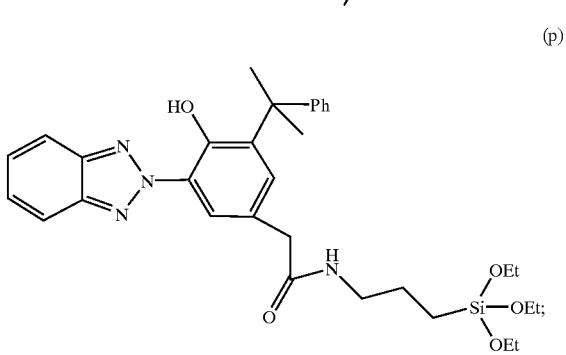

(p)

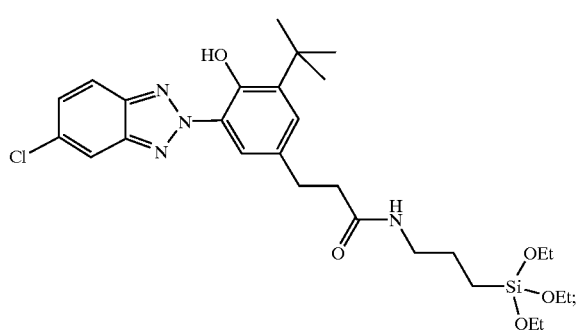

(q)

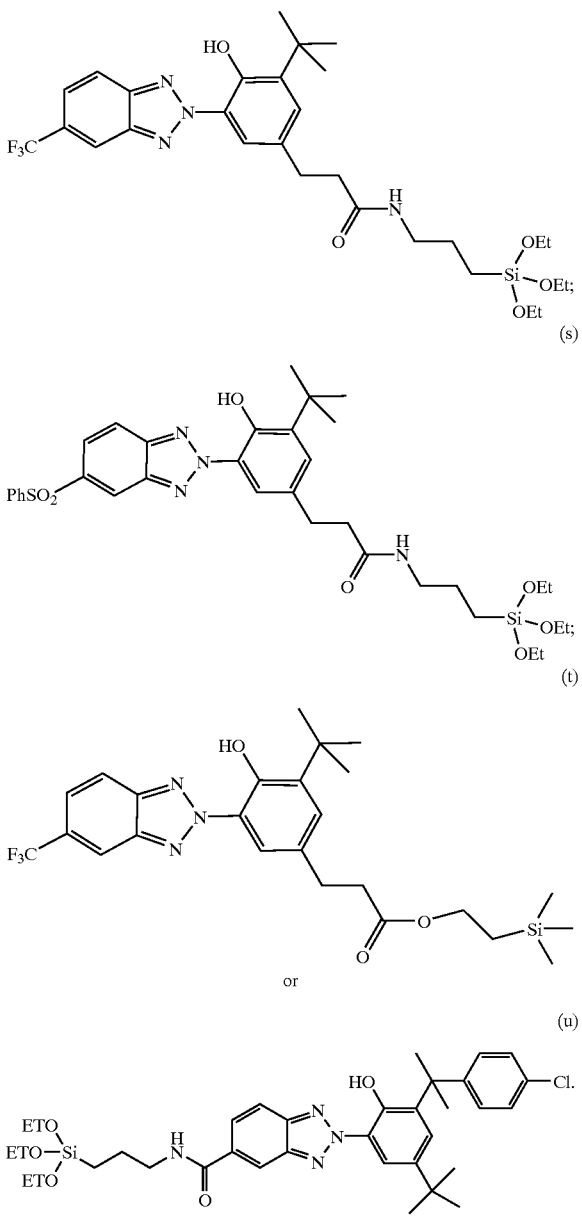

The instant invention also pertains to a composition stabilized against light-induced degradation which comprises,
(a) an organic material subject to light-induced degradation, and
(b) an effective stabilizing amount of a compound of formula (I) or (II).

Preferably, the organic material is a natural, semi-synthetic or synthetic polymer, especially a thermoplastic polymer.

Most preferably, the polymer is a polyolefin or polycarbonate, especially polyethylene or polypropylene; most especially polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalenedicarboxylate), or other blends or copolymers such as poly(ethylene/1,4-cyclohexylenedimethylene terephthalate) PETG or an ionomer.

Most especially, the polymer is a siloxane coating as a screening layer over polycarbonate.

In another preferred embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

Such automotive coatings are described in WO 92/20726; WO 92/05225 and by H. Furakawa et al., Progress in Organic Coatings, 24, 81–99 (1994) which describe the curing and properties of acrylosilane coatings.

Most preferably, the resin is a thermoset acrylic melamine resin or an acrylic urethane resin.

In yet another preferred embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula (I) or (II) can be incorporated into the carder material as early as the production of the latter, in the production of paper, for example, being added to the paper pulp. A second method of application is to spray the carder material with an aqueous solution of compounds of formula (I) or (II) or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula (I) or (II) can be easily incorporated into the coating composition.

The recording material according to this invention preferably contains 1 to 5000 mg/m$^2$, in particular 50–1200 mg/m$^2$, of a compound of formula (I) or formula (II).

As already mentioned, the recording materials according to the invention embrace a wide field. The compounds of formula (I) or (II) can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula (I) or (II) act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are preferably used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula (I) or (II) can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and pen-plotters. Of the above, recording materials for dye diffusion transfer printing are preferred, for example, as described in EP-A 507,734.

The instant compounds can also be employed in inks, preferably for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE). Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/iso-butylene copolymers, ethylene/but-1-ene copolymers, ethylene/hexene copolymers, ethylene/methylpentene copolymers, ethylene/heptene copolymers, ethyleneoctene copolymers, propylene/butadiene copolymers, isobutylene/isoprene copolymers, ethylene/alkyl acrylate copolymers, ethylenealkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid co-polymers (EAA), LLDPE/EVA, LLDPE/EAA and alternating or random polyalkylene/carbon mon-oxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrenelethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylo-nitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.
26. Crosslinked epoxy resins derived from polyepoxides, for example from bisglycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%. However, some high performance films or in UV absorbing layers of laminates such as those produced by coextrusion may contain from 5–15% by weight of the instant compounds. Concentrations of 5–10% by weight are typical in certain coextrusion applications.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated Monophenols, for Example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)4,6-dimethylphenol
2,6-di-octadecyl-4-methylphenol
2,4,6-tri-cyclohexylphenol
2,6-di-tert-butyl-4-methoxymethylphenol 1.2. Alkylated Hydroquinones, for Example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated Thiodiphenyl Ethers, for Example,
2,2'-thio-bis-(6-tert-butyl-4-methyl phenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for Example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)4-nonylphenol]
2,2'-methylene-bis-[6-(α,α-dimethylbenzyl)4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl Compounds, for Example,
1,3,5-tri-(3,5-di-tert-butyl-4-hydroxybenzyl)-2,4,6-trimethylbenzene di-(3,5-di-tert-butyl-4-hydroxybenzyl) sulfide 3,5-di-tert-butyl-4-hydroxybenzyl-mercapto-acetic acid isooctyl ester bis-(4-tert-butyl-3-hydroxy-2,6-dimethylbenzyl)dithiol terephthalate 1,3,5-tris-(3,5-di-tert-butyl-4-hydroxybenzyl) isocyanurate 1,3,5-tris-(4-tert-butyl-3-hydroxy-2,6-dimethylbenzyl) isocyanurate 3,5-di-tert-butyl-4-hydroxybenzyl-phosphoric acid dioctadecyl ester 3,5-di-tert-butyl-4-hydroxybenzyl-phosphoric acid monoethyl ester, calcium-salt 1.6. Acylaminophenols, for Example,
- 4-hydroxy-lauric acid anilide
- 4-hydroxy-stearic acid anilide
- 2,4-bis-octylmercapto-6-(3,5-tert-butyl-4-hydroxyanilino)-s-triazine
- octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic acid for example,
- N,N'-di-(3,5-di-tert-butyl-4-hydroxyphenylpropionyl)-hexamethylenediamine
- N,N'-di-(3,5-di-tert-butyl-4-hydroxyphenylpropionyl)-trimethylenediamine
- N,N'-di-(3,5-di-tert-butyl-4-hydroxyphenylpropionyl)-hydrazine 1.10 Diarylamines, for example,
- diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers 2.1. 2-(2'-Hydroxyphenyl)-benzotriazoles, for example, the 5'-methyl—, 3',5'-di-tert-butyl—, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol]such as the 1:1 or 1:2 complex, optionally with additional ligands such as n-butylamine, triethanolamine or N-cyclohexyl-diethanolamine, nickel dibutyidithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal—N'-salicyloyl-hydrazine, N,N'-bissalicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyidialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxyl-amine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl) benzofuran-2-one], 5,7-di-tert-butyl-3-(4-ethoxyphenyl) benzofuran-2-one, 3-(4-acetoxy-3,5-dimethylphenyl)-5,7-di-tert-butyl-benzofuran-2-one, 3-(3,5-di-methyl-4-pivaloyloxyphenyl)-5,7-di-tert-butyl-benzofuran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list), UV absorbers (item 2 of the list) and peroxide-destroying compounds (item 5 of the list).

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyunrate, 1,1,3,-tris(2-methyl-4-hydroxy-5-tert-butylphenyl)butane, 1,3,5-tris-[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzyl-phosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yl-n-dodecylsuccinimide, 1-acetyl-3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethyl-piperidin-4-yl) imino], 2,4,6-tris[N-(1-cyclohexyloxy-2,2,6,6-tetramethylpiperidin-4-yl)-n-butylamino]-s-triazine, and 1-(2-hydroxy-2-ethylpropoxy-4-octadecanoyloxy-2,2,6,6-tetramethyl-piperidine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino4,7-diazadecane, di-(1-octyloxy-2,2,6,6-tetramethyl-piperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethyl-piperidin-4-yl)-n-butylamino]-s-triazine, or 1-(2-hydroxy-2-ethylpropoxy-4-octadecanoyloxy-2,2,6,6-tetramethylpiperidine.

The instant composition can additionally contain another UV absorber selected from the group consisting of the benzotriazoles, s-triazines, the oxanilides, the benzylidene malonates, the hydroxybenzophenones, benzoates and the α-cyanoacrylates.

Particularly, the instant composition may additionally contain an effective stabilizing amount of at least one other 2-hydroxyphenyl-2H-benzotriazole; a tris-aryl-s-triazine; or a hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]phenyl}-2H-benzotriazole;

5-chloro-2-(2-hydroxy-3,5-di-tert-butylphenyl)-2H-benzotriazole;

5-chloro-2-(2-hydroxy-3-tert-butyl-5-methylphenyl)-2H-benzotriazole;

2-(2-hydroxy-5-tert-octylphenyl)-2H-benzotriazole;

2-{2-hydroxy-3-tert-butyl-5-[2-(octyloxy)carbonyl)ethyl]phenyl}2H-benzotriazole;

5-trifluoromethyl-2-(2-hydroxy-5-tert-octylphenyl)-2H-benzotriazole;

5-trifluoromethyl-2-(2-hydroxy-3,5di-tert-octylphenyl)-2H-benzotriazole;

2,2'-methylene-bis[6-(5-trifluoromethyl-2H-benzotriazol-2-yl)-4-tert-octylphenol];

methylene-2-[4-tert-octyl-6-(2H-benzotriazol-2-yl)phenol]2'-[4-tert-octyl-6-(5-trifluoro-methyl-2H-benzotriazol-2-yl)phenol];

3-(5-trifluoromethyl-2H-benzotriazol-2-yl)-5-tert-butyl-4-hydroxyhydrocinnamic acid;

methyl 3-(5-trifluoromethyl-2H-benzotriazol-2-yl)-5-tert-butyl-4-hydroxyhydrocinnamate;

isooctyl 3-(5-trifluoromethyl-2H-benzotriazol-2-yl)-5-tert-butyl-4-hydroxyhydrocinnamate;

5-trifluoromethyl-2-[2-hydroxy-5-(3-hydroxypropyl)phenyl]-2H-benzotriazole;

5-trifluoromethyl-2-[2-hydroxy-5-(3-acryloyloxypropyl)phenyl]-2H-benzotriazole;

5-trifluoromethyl-2-[2-hydroxy-5-(3-methacryloyloxypropyl)phenyl]-2H-benzotriazole;

5-trifluoromethyl-2-[2-hydroxy-5-(3-acrylylaminopropyl)phenyl]-2H-benzotriazole;

5-trifluoromethyl-2-[2-hydroxy-5-(3-methacrylylaminopropyl)phenyl]-2H-benzotriazole;

5-trifluoromethyl-2-(2-hydroxy-3-α-cumyl-5-tert-butylphenyl)-2H-benzotriazole;

5-trifluoromethyl-2-(2-hydroxy-3-α-cumyl-5-nonylphenyl)-2H-benzotriazole;

5-trifluoromethyl-2-[2-hydroxy-3-α-cumyl-5-(2-hydroxyethyl)phenyl]-2H-benzotriazole;

5-trifluoromethyl-2-[2-hydroxy-3-α-cumyl-5-(3-hydroxypropyl)phenyl]-2H-benzotriazole;

5-trifluoromethyl-2-(2-hydroxy-3,5-ditert-amylphenyl)-2H-benzotriazole;

5-trifluoromethyl-2-(2-hydroxy-3,5-ditert-butylphenyl)-2H-benzotriazole;

5-trifluoromethyl-2-(2-hydroxy-3-dodecyl-5-methylphenyl)-2H-benzotriazole;

5-trifluoromethyl-2-[2-hydroxy-3-tert-butyl-5-(3-hydroxypropyl)phenyl]-2H-benzotriazole;

5-trifluoromethyl-2-[2-hydroxy-3-tert-butyl-5-(2-hydroxyethyl)phenyl]-2H-benzotriazole;

5-trifluoromethyl-2-[2-hydroxy-5-(2-hydroxyethyl)phenyl]-2H-benzotriazole;

5-trifluoromethyl-2-(2-hydroxy-3,5-di-α-cumylphenyl)-2H-benzotriazole;

5-fluoro-2-(2-hydroxy-3,5-di-α-cumylphenyl)-2H-benzotriazole;

5-butylsulfonyl-2-(2-hydroxy-3,5-di-α-cumylphenyl)-2H-benzotriazole;

5-butylsulfonyl-2-(2-hydroxy-3,5-di-tert-butylphenyl)-2H-benzotriazole; and 5-butylsulfonyl-2-(2-hydroxy-3,5-di-tert-octylphenyl)-2H-benzotriazole.

Preferably, the tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine; and 2,4-bis(2,4-dimethylphenyl)-6-[2-hydroxy-4-(3-do-/tri-decyloxy-2-hydroxypropoxy)-phenyl]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylicimelamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be especially useful in other applications where their enhanced durability is required such as in solar films and the like.

The following examples are meant for illustrative purposes only and are not to be construed to limit the scope of the instant invention in any manner whatsoever.

EXAMPLE 1

5-Trifluoromethyl-2-(2-hydroxy-3-α-cumyl-5-tert-octylphenyl)-2H-benzotriazole a. Diazotization of 4-amino-3-nitro-benzotrifluoride To a 500 ml 3-necked flask, equipped with a mechanical stirrer, are added 41.2 g of 4-amino-3-nitro-benzotrifluoride, 52 ml of concentrated hydrochloride acid and 100 ml of distilled water. The stirred solution is cooled to 5° C and 17.3 g of sodium nitrite dissolved in 50 ml of water are added. The solution is stirred at 0 to 5° C. for two hours, then filtered and stored at −10° C.

b. Monoazo Adduct

To a 1000 ml flask, fitted with a mechanical stirrer, are added 40 g of sodium hydroxide dissolved in 200 ml of methanol and 32.4 g of 2-α-cumyl-4-tert-octylphenol in 50 ml of xylene. The solution is cooled to 5° C. and the diazo solution of 4-amino-nitro-benzotrifluoride prepared in part a. is added at 0 to 5° C. over a two-hour period. Then 100 ml of xylene are added and the organic layer is washed with water, aqueous hydrochloride acid, water, aqueous sodium bicarbonate solution and finally water. The solvent is removed under reduced pressure and the residue is purified by chromatography (silica gel, heptane:ethyl acetate 95:5) to yield 42.1 g of the adduct product as a dark red paste.

c. Reduction of the Monoazo Adduct

A 1000 ml flask is charged with 20 g of sodium hydroxide, 40 ml of water, 42.1 g of the monoazo adduct prepared in part b. and 400 ml of ethanol. The mixture is warmed to 80° C. and 27 g of formamidine sulfinic acid is added in portions with stirring. After 1.5 hours, the solution is cooled to room temperature and 100 ml of water are added. The pH is adjusted to pH 7 with concentrated hydrochloric acid. The ethanol is removed under vacuum and the water layer is extracted with methylene chloride. The solvent is then evaporated in vacuo and the residue is purified by chromatography (silica gel, heptane:tolunen 9:1) and crystallized from ethanol. The title compound is obtained in a yield of 5.6 g as a pale yellow solid melting at 119–121° C.

EXAMPLE 2

5-Trifluoromethyl-2-(2-hydroxy-5-tert-octylphenyl)-2H-benzotriazole

The title compound is prepared according to general procedure of Example 1 the diazo compound of 4-amino-3-nitrobenzotrifluoride and 4-tert-octylphenol, and which is purified by chromatography on silica gel. Recrystallization of the product from either heptane or methanol yields the title compound as a near white solid melting at 80–81° C.

EXAMPLE 3

5-Trifluoromethyl-2-(2-hydroxy-3-allyl-5-tert-octylphenyl)-2H-benzotriazole

The compound prepared in Example 2 (13.01 g, 0.033 mol), potassium hydroxide (2.37 g, 0.036 mol) and ethanol (60 mL) are charged to a reactor and stirred at ambient temperature for two hours. Allyl bromide (4.84 g, 0.039 mol) and potassium iodide (0.34 g, 0.002 mol) are added to the reaction mixture which is heated to 85° C. After holding at 85° C. for 4.5 hours, the solvent is removed and replaced with 100 mL of heptane. The mixture is washed thrice with 40 mL of water. The solvent is then removed to yield 14.2 g of the corresponding O-allyl ether as an off-white solid.
Analysis:
$^1$Hnmr (CDCl$_3$): δ 0.78 (s, 9H), 1.41 (s, 6H), 1.77 (s, 2H), 4.60–4.65 (d, 2H), 5.16–5.34 (m, 2H), 5.86–6.00 (m, 1H), 7.06–7.11 (d, 1H), 7.49–7.54 (dd, 1H), 7.61–7.67 (m, 2H), 8.08–8.12 (d, 1H), 8.35 (s, 1H)

The O-allyl compound (14.2 g) as prepared above is charged to a reactor and heated to 190–195° C. and held at that temperature for five hours. Flash column chromatography with silica gel and ethyl acetate/heptane solvent as eluent to give the title compound in 12.2 g yield as a yellow oil.
Analysis:
Mass spectrometry: 432 (M+H);
$^1$Hnmr (CDCl$_3$): δ 0.78 (s, 9H), 1.46 (s, 6H), 1.81 (s, 2H), 3.53–3.64 (d, 2H), 5.06–5.20 (m, 2H), 6.02–6.18 (m, 1H), 7.29–7.34 (d, 1H), 7.66–7.72 (dd, 1H), 8.05–8.12 (d, 1H), 8.29–8.35 (m, 2H), 11.17 (s, 1H)

EXAMPLE 4

5-Trifluoromethyl-2-[2-hydroxy-3-(3-triethoxysilyl) propyl-5-tert-octylphenyl]-2H-benzotriazole The title compound is prepared by the procedure of Example 3 of U.S. Pat. No. 5,391,795 using 5-trifluoromethyl-2-(2-hydroxy-3-allyl-5-tert-octylphenyl)-2H-benzotriazole prepared in Example 3 above, Karstedt's catalyst (complex of divinyltetramethyidisiloxane with platinum) and triethoxysilane. It is isolated as a viscous yellow oil.
$^{29}$Si NMR (CDCl$_3$, 500 MHz, Cr(AcAc)$_2$): −44.78 ppm.
$^1$H NMR (CDCl$_3$, 500 MHz): δ 11.50 (s, 1H), 8.32 (d, 1H), 8.27 (d, 1H), 8.09 (d, 1H), 7.69 (dd, 1H), 7.31 (d, 1H), 3.83 (q, 6H), 2.83 (t, 2H), 1.84 (quintet, 2H), 1.80 (s, 2H), 1.45 (s, 6H), 1.22 (t, 9H), 0.78 (s, 9H), 0.76 (t, 2H).
$^{19}$F NMR (CDCl$_3$, 500 MHz, CF$_3$COOH): −68.88 ppm.

EXAMPLE 5

Methyl 3-(Trifluoromethyl-2H-benzotriazol-2-yl)-5-tert-butyl-4-hydroxyhydrocinnamate The general procedure of Example 1, parts a and b, is followed to prepare the unisolated, solid, monoazo intermediate of the title compound from 62.5 g of 4-amino-3-nitrobenzotrifluoride (=4-trifluoromethyl-o-nitroaniline).

The monoazo intermediate (84 g, 0.19 mol), xylenes (116 g, 1.08 mol), diethylamine (100 g, 1.4 mol) and 5% palladium on charcoal (0.5 g, 50% assay) are charged to a reactor. Hydrazine (27.4 g, 0.56 mol) is dripped in over a two-hour period at a temperature range of 15–45° C. After the addition is complete, the temperature is raised to 80° C. and held there for three hours. The reaction is judged complete by thin layer chromatography. The catalyst is removed by filtration and the solvent removed in vacuo to yield 36 grams of the product. After recrystallization from methanol, the title compound is obtained as light yellow needles melting at 105–107° C.
Analysis:
Mass spectrometry: 422 (M+H);
$^1$Hnmr (CDCl$_3$): δ 1.51 (s, 9H), 2.71 (t, 2H), 3.02 (t, 2H), 3.71 (s, 3H), 7.26 (d, 1H), 7.69 (dd, 1H), 8.07 (d, 1H), 8.17 (d, 1H), 11.55 (s, 1H)

EXAMPLE 6

5-Trifluoromethyl-2-[2-hydroxy-3-tert-butyl-5-(3-hydroxypropyl)phenyl]-2H-benzotriazole The title compound is prepared by reacting the ester compound of Example 5 with lithium aluminum hydride according to the procedure of Example 19 of U.S. Pat. No. 5,280,124. The title compound is obtained in 80% yield as a solid melting at 90–91° C.
Analysis:
$^1$Hnmr (CDCl$_3$): δ 1.51 (s, 9H), 1.95 (m, 2H), 2.75 (t, 2H), 3.75 (t, 2H), 7.26 (d, 1H), 7.65 (dd, 1H), 8.05 (d, 1H), 8.14 (d, 1H), 8.26 (s, 1H)

EXAMPLE 7

5-Trifluoromethyl-2-[2-hydroxy-3-tert-butyl-5-(3-allyl-carbamoyloxy)propylphenyl]-2H-benzotriazole The title compound is prepared by reacting a stoichiometric amount of the compound prepared in Example 6 with allyl isocyanate.

EXAMPLE 8

5-Trifluoromethyl-2-{2-hydroxy-3-tert-butyl-5-[3-(3-triethyoxysilyl)propyl-carbamoyloxy)propyl]phenyl}-2H-benzotriazole The title compound is prepared by reacting the allyl compound of Example 7 with triethoxysilane according to the procedure of Example 4.

EXAMPLE 9

5-Trifluoromethyl-2-[2-hydroxy-3-tert-butyl-5-(2-hydroxyethyl)phenyl]-2H-benzotriazole When using the general procedure of Example 1 the 2-α-cumyl-4-tert-octylphenol is replaced by 2-tert-butyl-4-(2-hydroxyethyl)phenol, the title compound is prepared.

EXAMPLE 10

5-Trifluoromethyl-2-[2-hydroxy-3-tert-butyl-5-(2-allylcarbamoyloxy)ethylphenyl]-2H-benzotriazole The title compound is prepared by the reaction of a stoichiometric amount of the compound prepared in Example 9 with allyl isocyanate.

EXAMPLE 11

5-Trifluoromethyl-2-{2-hydroxy-3-tert-butyl-5-[2-(3-triethyoxysilyl)propyl-carbamoyloxy)ethyl]phenyl}-2H-benzotriazole The title compound is prepared by the reaction of the compound prepared in Example 10 with triethoxysilane according to the procedure of Example 4.

EXAMPLE 12

5-Trifluoromethyl-2-[2-hydroxy-5-(2-hydroxyethyl) phenyl]-2H-benzotriazole

When using the general procedure of Example 1, the 2-α-cumyl-4-tert-octyl phenol is replaced by 4-(2-hydroxyethyl)phenol, the title compound is prepared.

EXAMPLE 13

5-Trifluoromethyl-2-[2-hydroxy-5-(2-allylcarbamoyloxy)ethylphenyl]-2H-benzotriazole The title compound is prepared by the reaction of a stoichiometric amount of the compound prepared in Example 12 with allyl isocyanate.

EXAMPLE 14

5-Trifluoromethyl-2-{2-hydroxy-5-[2-(3-triethyoxysilyl)propyl-carbamoyloxy)ethyl]phenyl}-2H-benzotriazole The title compound is prepared by the reaction of the compound prepared in Example 13 with triethoxysilane according to the procedure of Example 4.

EXAMPLE 15

5-Trifluoromethyl-2-[2-hydroxy-3-α-cumyl-5-(2-hydroxyethyl)phenyl]-2H-benzotriazole When using the general procedure of Example 1 the 2-α-cumyl-4-tert-octylphenol is replaced by 2-α-cumyl-4-(2-hydroxyethyl)phenol, the title compound is prepared.

EXAMPLE 16

5-Trifluoromethyl-2-[2-hydroxy-3-α-cumyl-5-(2-allylcarbamoyloxy)ethylphenyl]-2H-benzotriazole The title compound is prepared by the reaction of a stoichiometric amount of the compound prepared in Example 15 with allyl isocyanate.

EXAMPLE 17

5-Trifluoromethyl-2-{2-hydroxy-3-α-cumyl-5-[2-(3-triethyoxysilyl)propyl-carbamoyloxy)ethyl]phenyl}-2H-benzotriazole The title compound is prepared by the reaction of the compound prepared in Example 16 with triethoxysilane according to the procedure of Example 4.

EXAMPLE 18

5-Trifluoromethyl-2-[2-hydroxy-3-(3-diethoxymethylsilyl)propyl-5-tert-octylphenyl]-2H-benzotriazole The title compound is prepared by the procedure of Example 1 of U.S. Pat. No. 5,679,820 using 5-trifluoromethyl-2-(2-hydroxy-3-allyl-5-tert-octyl-phenyl)-2H-benzotriazole prepared in Example 3 above, Karstedt's catalyst (complex of divinyl-tetramethyldisiloxane with platinum) and diethoxymethyl-silane.

Quite analogously to the compounds listed in the tables below, one can start with triphenylsilane, tribenzylsilane, other trialkylsilanes, trialkoxysilanes, dialkoxyalkylsilanes, alkoxydialkylsilanes, and the similar silane intermediates to prepare the corresponding silylated benzotriazole compounds.

EXAMPLES 19–42

Using the reaction conditions similar to those described in Example 18, compounds of formula III are prepared:

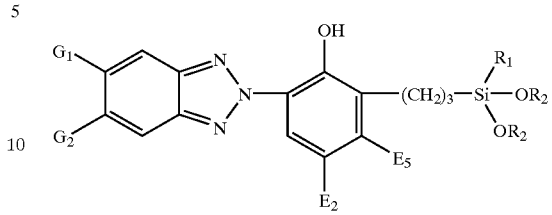

(III)

| Example | $G_1$ | $G_2$ | $E_2$ | $R_1$ | $R_2$ |
|---|---|---|---|---|---|
| 19 | H | $CF_3$ | α-cumyl | methyl | ethyl |
| 20 | Cl | $CF_3$ | α-cumyl | methyl | ethyl |
| 21 | F | $CF_3$ | dodecyl | methyl | ethyl |
| 22 | F | F | methyl | methyl | ethyl |
| 23 | Cl | Cl | tert-octyl | methyl | ethyl |
| 24 | F | Cl | dodecyl | methyl | ethyl |

For each of the compounds of Examples 19–24, $E_5$ is hydrogen.

| Example | $G_2$ | $E_3$ | $E_2$ | $R_1$ | $R_2$ |
|---|---|---|---|---|---|
| 25 | $E_3SO_2$ | ethyl | tert-butyl | methyl | ethyl |
| 26 | $E_3SO_2$ | n-butyl | tert-octyl | n-butyl | ethyl |
| 27 | $E_3SO_2$ | n-butyl | dodecyl | methyl | phenyl |
| 28 | $E_3SO_2$ | ** | tert-butyl | hexyl | hexyl |
| 29 | $E_3SO_2$ | phenyl | methyl | methyl | ethyl |
| 30 | $E_3SO_2$ | dodecyl | tert-butyl | methyl | ethyl |
| 31 | —PO(C_6H_5)_2 | — | tert-butyl | methyl | ethyl |

** is $CH_3OCO—CH_2CH_2—$

For each of the compounds of Examples 25–31, $G_1$ and $E_5$ are both hydrogen.

| Example | $G_2$ | $G_3$ | $E_2$ | $R_1$ | $R_2$ |
|---|---|---|---|---|---|
| 32 | —COOG_3 | methyl | α-cumyl | methyl | ethyl |
| 33 | —COOG_3 | cyclohexyl | methyl | methyl | ethyl |
| 34 | —COOG_3 | dodecyl | α-cumyl | methyl | ethyl |
| 35 | —CONHG_3 | hexyl | $CH_2CH_2OH$ | methyl | ethyl |
| 36 | —CON(G_3)_2 | butyl | methyl | methyl | ethyl |
| 37 | phthalimido | — | octyl | methyl | ethyl |

For each of the compounds of Examples 32–37, $G_1$ and $E_5$ are both hydrogen.

| Example | $G_2$ | $E_2$ | $E_5$ | $R_1$ | $R_2$ |
|---|---|---|---|---|---|
| 38 | $CF_3$ | dodecyl | methoxy | methyl | ethyl |
| 39 | $CF_3$ | butyl | octoxy | methyl | ethyl |
| 40 | $CF_3$ | octyl | NH—CO—CH_3 | methyl | ethyl |
| 41 | $CF_3$ | methyl | NHCO-octyl | methyl | ethyl |
| 42 | $CF_3$ | dodecyl | NH—CH_3 | methyl | ethyl |

For each of the compounds of Examples 38–42, $G_1$ is hydrogen.

EXAMPLES 43–61

For Examples 43–46, these materials are prepared by a method analogous to the method of Example 5b of U.S. Pat. No. 5,185,445 where the appropriate substituted benzotriazole is dissolved in toluene and is heated to 100° C. with the hydroxy-substituted alkyl-silane or alkyl-siloxane in the presence of dibutyltin oxide for form the title compound.

For Examples 47–48, these materials are prepared where the appropriate substituted benzotriazole is added to the reaction flask alone with the amino-substituted alkyl-silane or alkyl-siloxane and heated to 120° C. A slight vacuum is applied to facilitate removal of the methanol by-product to give the title compound.

For Examples 49–52, the compounds are made by a method analogous to that of Example 6 of U.S. Pat. No. 5,185,445 where a suspension of the appropriate benzotriazole starting material and 3-chloropropyl diethoxymethylsilane or related silane and potassium carbonate in anhydrous N,N-dimethylacetamide is heated to 100° C. to yield the desired compounds.

For Example 53, the appropriate intermediate benzotriazole is made by the procedure of Example 10. The intermediate is then hydrosilylated with diethoxymethylsilane using the experimental conditions of Example 4 to give the desired compound.

The compounds of Examples 54–58 are prepared in several steps. The first intermediate benzotriazole is made by the method of Example 1, but instead of using 2-α-cumyl-4-tert-octyl-phenol, the Michael adduct of resorcinol and methyl acrylate is used to give the desired compound. The second intermediate is then made by reacting the first intermediate benzotriazole with α-methylstyrene in the presence of p-toluenesulfonic acid. The next intermediate compound is prepared by reacting the second intermediate in a manner analogous to Example 30 of British 2,319,035A. The next intermediate is made by reacting the last intermediate benzotriazole with allyl alcohol in the presence of toluene solvent. Finally, the allyl substituted benzotriazole is reacted with diethoxymethylsilane using the conditions of Example 4.

The compounds of Examples 59–62 are also prepared in several steps. The first intermediate is made by a method analogous to that of Example 3. In the next step this intermediate benzotriazole is hydroboration conditions as described by Brown in "Boranes in Organic Chemistry", Cornell University Press, Ithaca, N.Y. 1972; and by J. March in "Advanced Organic Chemistry", 2nd Edition, McGraw-Hill, New York, 1977, page 718. This intermediate is reacted by the procedure of Example 10 by reacting the 2-(3-hydroxypropyl) substituted benzotriazole with allyl isocyanate. The title compound is prepared by the allyl urethane intermediate by reaction with diethoxymethylsilane according to the method of Example 4.

Following the general methods described above, compounds of formula (IV) or (V) are prepared.

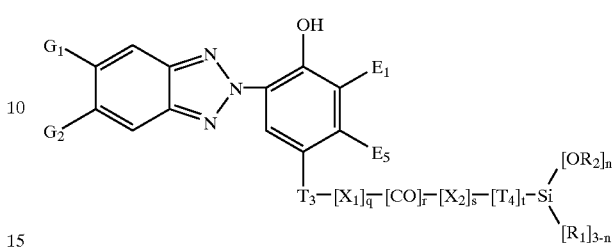

(IV)

| *Ex | $G_1$ | $G_2$ | $E_1$ | $T_3/T_4$ | $X_2$ | n | $R_1$ | $R_2$ |
|---|---|---|---|---|---|---|---|---|
| 43 | H | $CF_3$ | Cu | $(CH_2)_2/(CH_2)_3$ | —O— | 3 | Me | Et |
| 44 | H | $CF_3$ | Cu | $(CH_2)_2/(CH_2)_3$ | —O— | 2 | Me | Et |
| 45 | H | $CF_3$ | Cu | $(CH_2)_2/(CH_2)_3$ | —O— | 1 | Me | Et |
| 46 | H | $CF_3$ | Cu | $(CH_2)_2/(CH_2)_3$ | —O— | 0 | Me | Et |
| 47 | H | $CF_3$ | tBu | $(CH_2)_2/(CH_2)_4$ | —NH— | 1 | Me | Me |
| 48 | Cl | Cl | tBu | $(CH_2)_2/(CH_2)_3$ | —NH— | 2 | Me | Et |

*In the compounds of Examples 43–58, tBu is tert-butyl, Cu is α-cumyl, Et is ethyl and Me is methyl.

In each of compounds 43–48, $E_5$ is hydrogen; q is 0 and r, s and t are each 1. When q, r, s and/or t equal 0, this indicates a direct bond.

| *Ex | $G_2$ | $E_1$ | $T_3/T_4$ | $X_1$ | $X_2$ | r | s |
|---|---|---|---|---|---|---|---|
| 49 | F | tBu | $(CH_2)_3/(CH_2)_3$ | —O— | — | 0 | 0 |
| 50 | ** | Cu | $(CH_2)_3/(CH_2)_3$ | —O— | — | 0 | 0 |
| 51 | ** | tBu | $(CH_2)_3/(CH_2)_3$ | —O— | — | 0 | 0 |
| 52 | ** | tBu | $(CH_2)_3/(CH_2)_3$ | —NH— | — | 0 | 0 |
| 53 | CN | tBu | $(CH_2)_2/(CH_2)_3$ | —O— | —NH— | 1 | 1 |

*In the compounds of Examples 49–53, tBu is tert-butyl and Cu is α-cumyl.

In compound 50,  denotes butyl—$SO_2$—; in compound 51,  denotes phenyl—$SO_2$—; and in compound 52, ** denotes dodecyl—$SO_2$—.

In each of compounds 49–53, $E_5$ is hydrogen; q and t are each 1; $R_1$ is methyl; $R_2$ is ethyl; $G_1$ is hydrogen; and n is 2.

| Example | $G_2$ | $E_1$ | $E_5$ | $X_2$ | n |
|---|---|---|---|---|---|
| 54 | $CF_3$ | α-cumyl | methoxy | —O— | 2 |
| 55 | $CF_3$ | α-cumyl | octyloxy | —O— | 1 |
| 56 | $CF_3$ | t—butyl | $NHCOCH_3$ | —NH— | 2 |
| 57 | ** | α-cumyl | $NHCOC_8H_{17}$ | —NH— | 1 |
| 58 | $COOCH_3$ | α-cumyl | hydrogen | —NH— | 2 |

In compound 57, ** denotes phenyl—$SO_2$—.

In each of compounds 54–58, $G_1$ is hydrogen; $T_3$ is ethylene; $T_4$ is trimethylene; q is 0; r, s and t are each 1; $R_1$ is methyl; and $R_2$ is ethyl.

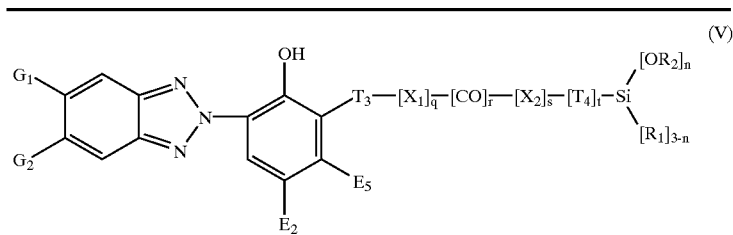

(V)

| Example | $G_1$ | $G_2$ | $E_2$ | $T_3$ | $T_4$ |
|---|---|---|---|---|---|
| 59 | F | F | α-cumyl | $(CH_2)_3$ | $(CH_2)_3$ |
| 60 | H | $CF_3$ | methyl | $(CH_2)_3$ | $(CH_2)_3$ |
| 61 | H | $CF_3$ | t-octyl | $(CH_2)_3$ | $(CH_2)_3$ |

In each of compounds 59–61, $E_5$ is hydrogen; $X_1$ is —O—; $X_2$ is —NH—; q, r, s and t are each 1; n is 2; $R_1$ is methyl; $R_2$ is ethyl; and $G_1$ is hydrogen.

EXAMPLES 62–75

For Examples 62–75, the appropriate substituted benzotriazole are prepared according to the general methods of Example 29 of British 2,319,035A and instant Example 54. The intermediate is reacted with allyl bromide dissolved in ethanol in the presence of potassium hydroxide and potassium iodide. In the case of Example 66, 6-bromohex-1-ene is substituted for allyl bromide. The unsaturated intermediate formed is hydrosilylated with the appropriate substituted silane using the conditions of Example 4.

Following the general method described above, compounds of formula VI are prepared.

EXAMPLES 76–92

For Examples 76–85, these compounds are prepared by essentially the same synthetic scheme. A typical synthesis for the compound of Example 77 is outlined below.

5-Carbomethoxy-2-(2-hydroxy-3-α-cumyl-5-tert-octylphenyl)-2H-benzotriazole, synthesized as seen in Example 36 of British 2,319,035A, is transesterified with excess 1,4-butanediol in the presence of p-toluenesulfonic acid. This intermediate is reacted with allyl isocyanate according to the method of Example 10. The title compound is prepared with the allyl urethane substituted benzotriazole intermediate prepared above with diethoxymethylsilane using the conditions of instant Example 4.

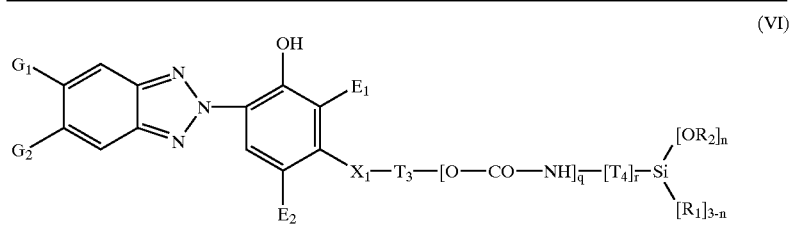

(VI)

| *Ex | $G_2$ | $E_1$ | $E_2$ | $T_3/T_4$ | q | r | n | X |
|---|---|---|---|---|---|---|---|---|
| 62 | F | Cu | Me | $(CH_2)_3$/— | 0 | 0 | 2 | —O— |
| 63 | Cl | tBu | tOc | $(CH_2)_3$/— | 0 | 0 | 1 | —O— |
| 64 | Cl | Do | Me | $(CH_2)_3$/— | 0 | 0 | 2 | —O— |
| 65 | $CF_3$ | Cu | tBu | $(CH_2)_3$/— | 0 | 0 | 2 | —O— |
| 66 | $CF_3$ | tBu | tBu | $(CH_2)_6$/— | 0 | 0 | 3 | —O— |
| 67 | $CF_3$ | Cu | tBu | $(CH_2)_3$/— | 0 | 0 | 0 | —O— |
| 68 | ** | Cu | tBu | $(CH_2)_3$/— | 0 | 0 | 2 | —O— |
| 69 | ** | tBu | Do | $(CH_2)_3$/— | 0 | 0 | 2 | —O— |
| 70 | ** | Cu | Me | $(CH_2)_3$/— | 0 | 0 | 1 | —O— |
| 71 | *** | Cu | tBu | $(CH_2)_3$/— | 0 | 0 | 2 | —O— |
| 72 | $CF_3$ | Cu | Me | $(CH_2)_3$/$(CH_2)_3$ | 1 | 1 | 2 | —O— |
| 73 | $CF_3$ | tBu | Do | $(CH_2)_3$/$(CH_2)_3$ | 1 | 1 | 1 | —O— |
| 74 | $CF_3$ | Cu | Me | $(CH_2)_3$/— | 0 | 0 | 2 | —NH— |
| 75 | $CF_3$ | tBu | tBu | $(CH_2)_3$/$(CH_2)_3$ | 1 | 1 | 2 | —NH— |

*tBu is tert-butyl, Cu is α-cumyl, Do is dodecyl, Me is methyl and tOc is tert-octyl.
For each of the compounds of Examples 62 to 75, $R_1$ is methyl and $R_2$ is ethyl; and $G_1$ is hydrogen except for compound 64 where $G_1$ is fluoro.
For compound 68,  denotes phenyl-$SO_2$—; for compound 69  denotes n-butyl-$SO_2$—; and for compound 70, ** denotes dodecyl-$SO_2$—.
For compound 71, *** denotes $(C_6H_5)_2PO$—.

For Examples 86–92, these compounds are prepared similarly to those for Examples 76–85. The intermediate needed is prepared as described above for Example 77 except that the transesterification is carried out with allyl alcohol instead of butylene glycol.

Following the general method described above, compounds of formula VII are prepared.

USSR, 26, 3111 (1956). The allyl substituted bis-benzotriazole formed is then silylated according to the procedure of Example 4 with diethoxymethylsilane.

Following the general method described above, compounds of formula VIII are prepared.

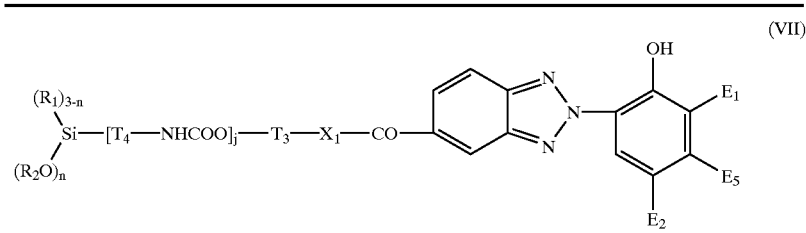

(VII)

| *Ex | $E_1$ | $E_2$ | $E_5$ | $T_3/T_4$ | $R_1$ | $R_2$ | n | $X_1$ |
|---|---|---|---|---|---|---|---|---|
| 76 | Cu | Me | H | $(CH_2)_2/(CH_2)_3$ | Me | Et | 3 | —O— |
| 77 | Cu | tOc | H | $(CH_2)_4/(CH_2)_3$ | Me | Et | 2 | —O— |
| 78 | tBu | tBu | H | $(CH_2)_6/(CH_2)_6$ | Me | Et | 2 | —NH— |
| 79 | Cu | Cu | H | $(CH_2)_3/(CH_2)_3$ | Me | Bu | 0 | —O— |
| 80 | Cu | Cu | $OCH_3$ | $(CH_2)_3/(CH_2)_3$ | Me | Et | 1 | —O— |
| 81 | Cu | Cu | OOc | $(CH_2)_3/(CH_2)_3$ | Me | Et | 2 | —NH— |
| 82 | Do | Do | | $NHCOOc/(CH_2)_4/(CH_2)_3$ | Me | Et | 1 | —O— |
| 83 | Cu | tOc | | $NHCOMe/(CH_2)_4/(CH_2)_3$ | Me | Et | 2 | —O— |
| 84 | Cu | tBu | | $NHCOMe/(CH_2)_4/(CH_2)_3$ | Et | Et | 3 | —NH— |
| 85 | Cu | Do | H | $(CH_2)_4(CH_2)_3$ | He | Bu | 2 | —O— |

*Bu is butyl, tBu is tert-butyl, Cu is α-cumyl, Do is dodecyl, Et is ethyl, He is hexyl, Me is methyl, Oc is octyl and tOc is tert-octyl.
For each of the compounds of Examples 76 to 85, j is 1.

| *Ex | $E_1$ | $E_2$ | $E_5$ | $T_3$ | $R_2$ | $R_1$ | n | X |
|---|---|---|---|---|---|---|---|---|
| 86 | Cu | tOc | H | $(CH_2)_3$ | Me | Et | 2 | —O— |
| 87 | tBu | tBu | H | $(CH_2)_3$ | Me | Et | 3 | —NH— |
| 88 | Cu | Me | H | $(CH_2)_6$ | Bu | Bu | 1 | —O— |
| 89 | Cu | Cu | $OCH_3$ | $(CH_2)_3$ | Me | Et | 2 | —O— |
| 90 | Cu | Cu | $OC_8H_{17}/(CH_2)_3$ | | Me | Et | 2 | —O— |
| 91 | Cu | Cu | $NHCOOc/(CH_2)_3$ | | Me | Et | 1 | —O— |
| 92 | H | H | $NHCOOc/(CH_2)_3$ | | Me | Et | 0 | —O— |

*Bu is butyl, tBu is tert-butyl, Cu is α-cumyl, Et is ethyl, Me is methyl, Oc is octyl and tOc is tert-octyl.
For each of the compounds of Examples 86 to 92, j is 0 and there is no $T_4$ moiety.

EXAMPLES 93–106

Since the compounds of Examples 96–106 are prepared by essentially the same synthetic route, the preparation of the compound of Example 98 is outlined below.

Using the Mannich base type conditions as outlined in copending application Ser. No. 09/234,880 at Examples 34–35, the Mannich base of 2-(2-hydroxy-5-methylphenyl)-2H-benzotriazole is reacted with methyl 3-(5-trifluoromethyl-2H-benzotriazol-2-yl)4-hydroxyhydrocinnamate to form a ester substituted bis-benzotriazole intermediate. This ester intermediate product is reduced with lithium aluminum hydride to form the corresponding alcohol substituted benzotriazole according to the procedure of Example 19 of U.S. Pat. No. 5,280,124. The hydroxyalkyl intermediate form is transformed into the corresponding alkene by refluxing with phosphorus tribromide in pyridine. Similar procedures are taught by G. I. Samokhvalov et al., Proc. Acad. Sci. USSR, 84, 1179 (1952) and J. Gen. Chem.

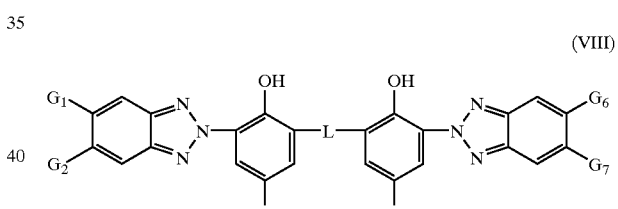

(VIII)

At least one of $G_2$, $G_7$, $E_2$ or $E_9$ contain a group A or group B.

A is $-T_1-[X]_q-[CO]_r-[X_2]_s-[T_2]_t-Si(OR_2)_n(R_1)_{3-n}$.

B is $-CO-X-T_1-[OCO-NH-T_2]_j-Si(OR_2)_n(R_1)_{3-n}$ where j is 0 or 1.

| Example | $G_2$ | $G_7$ | $E_2$ | $E_9$ | n |
|---|---|---|---|---|---|
| 93 | $CF_3$ | $CF_3$ | A | A | 3 |
| 94 | $C_6H_5SO_2$ | $C_6H_5SO_2$ | A | A | 2 |
| 95 | $C_4H_9SO_2$ | $C_4H_9SO_2$ | A | A | 2 |
| 96 | Cl | Cl | A | A | 0 |
| 97 | F | F | A | A | 1 |
| 98 | $CF_3$ | H | A | $CH_3$ | 2 |

In Examples 93–98, $G_1$ and $G_6$ are each hydrogen; $T_1$ is trimethylene; $R_1$ is methyl; $R_2$ is ethyl; q, r, s and t are each 0; and L is methylene.

| Example* | G₂ | G₇ | E₂ | E₉ | n |
|---|---|---|---|---|---|
| 99 | C₆H₅SO₂ | H | A | tOc | 2 |
| 100 | CN | H | A | tBu | 0 |
| 101 | CH₃COO | H | A | Do | 1 |
| 102 | H | H | Me | A | 2 |
| 103 | H | Cl | Me | A | 3 |

*In the compounds of Examples 99–103, tBu is tert-butyl, Do is dodecyl; Me is methyl and tOc is tert-octyl.
In Examples 99–103, $G_1$ and $G_6$ are each hydrogen; $T_1$ is ethylene; $T_2$ is trimethylene; $R_1$ is methyl; $R_2$ is ethyl; r, s and t are each 1; and L is methylene.
In Example 99, $X_2$ is —O—; and q is 0; in Example 100, X is —O— and $X_2$ is —NH—, and q is 1; in Example 101, X is —NH— and $X_2$ is —O—, and q is 1; in Example 102, $X_2$ is —O—, and q is 0.

| Example* | G₂ | G₇ | E₂ | E₉ | n |
|---|---|---|---|---|---|
| 104 | Cl | H | B | Me | 2 |
| 105 | B | Cl | Me | Me | 2 |
| 106 | B | H | tOc | tOc | 0 |

*In the compounds of Examples 104–106, Me is methyl and tOc is tert-octyl.
In Example 104, $G_1$ is chloro; $G_6$ is hydrogen; $T_1$ is trimethylene; X is —O—; $R_1$ and $R_2$ are each butyl; j is 0 and L is methylene.
In Example 105, $G_1$ and $G_6$ are each hydrogen; $T_1$ and $T_2$ are each trimethylene; X is —NH—; $R_1$ is methyl; $R_2$ is ethyl; j is 1 and L is methylene.
In Example 106, $G_1$ and $G_6$ are each hydrogen; $T_1$ is trimethylene; X is —O—; $R_1$ is methyl; $R_2$ is ethyl; j is 0 and L is methylene.

Comparative Example 1

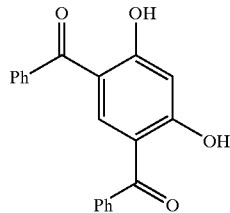

This hydroxybenzophenone compound is prepared according to Example 1 of U.S. Pat. No. 5,391,795. U.S. Pat. No. 5,391,795 is incorporated herein by reference.

Comparative Example 2

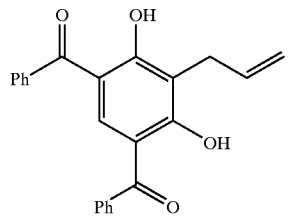

This allyl-substituted hydroxybenzophenone compound is prepared according to Example 2 of U.S. Pat. No. 5,391,795.

Comparative Example 3

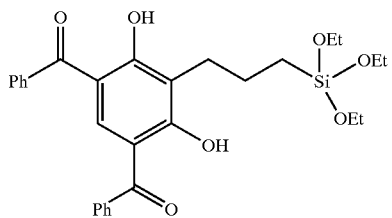

This triethoxysilylpropyl-substituted hydroxybenzophenone compound is prepared according to Example 3 of U.S. Pat. No. 5,391,795.

Comparative Example 4

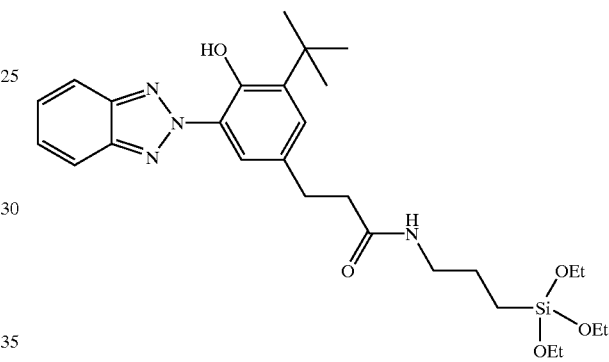

3-(2H-Benzotrazol-2-yl)-5-t-butyl-4-hydroxyhydrocinnamic acid (5 g, 0.0146 mol), toluene (100 g, 1.08 mol), thionyl chloride (2.55 g, 0.0209 mol) and DMF (0.1 g, 0.0014 mol) are added to a reaction flask and heated to 90° C. After 30 minutes, the excess thionyl chloride and 50 g of toluene are distilled away. The resultant solution is added to an addition funnel and is added to a solution of H₂N(CH₂)₃Si(OEt)₃ (3.88 g, 0.0175 mol), toluene (50 g, 0.54 mol) and triethylamine (100 g, 0.98 mol) at ambient temperature. After addition is complete (ca. 30 minutes), the slurry is heated to 75° C. for 90 minutes. The salt is filtered and the solvents are distilled off. The resulting oil is chromatographed on silica gel with ethyl acetate/heptane (1:1) as the eluent. The desired product is obtained as a light yellow solid (6.4 g);

mp 90–95° C.

¹H NMR (500 MHz, CDCl₃): δ 11.80 (s, 1H), 8.15 (d, 1H), 7.94(m, 2H), 7.49(m, 2H), 7.22(d, 1H), 5.73 (broad t, 1H), 3.80 (q, 6H), 3.27 (q, 2H), 3.02 (t, 2H), 2.52(t, 2H), 1.61 (quintet, 2H), 1.50 (s, 9H), 1.21 (t, 9H), 0.60 (t, 2H).

²⁹Si NMR (500 MHz, CDCl₃, Cr(AcAc)₂): −45.4 ppm.

Mass spec: M/Z=542

Comparative Example 5

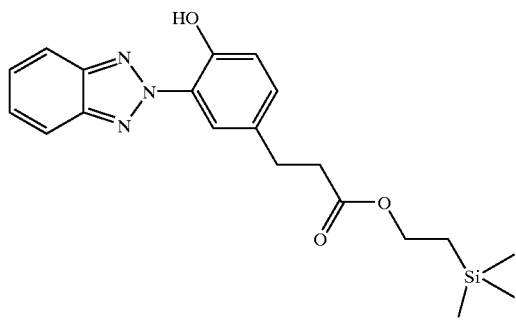

Methyl 3-(2H-benzotriazol-2-yl)-4-hydroxyhydrocinnamate (12 g, 0.04 mol), HO(CH$_2$)$_2$Si(CH$_3$)$_3$ (5 g, 0.042 mol), dibutyl tin oxide (3.7 g, 0.015 mol), and toluene (54 g, 0.59 mol) are added to a reaction flask and heated to 100° C. After 17 hours, the solvent is distilled off and the resulting oil is chromatographed on silica gel with heptane/ethyl acetate (9:1) as the eluent. The desired product is obtained (12 g) as a white solid;

mp 73–75° C.

$^{29}$Si NMR (500 MHz, CDCl$_3$, Cr(AcAc)$_2$): 0.15 ppm.

$^1$H NMR (500 MHz, CDCl$_3$): δ 11.20 (s, 1H), 8.25 (d, 1H), 7.94 (m, 2H), 7.49 (m, 2H), 7.25 (d, 1H), 7.15 (d, 1H), 4.20 (t, 2H), 3.00 (t, 2H), 2.65 (t, 2H), 1.00 (t, 2H), 0.15 (s, 9H).

Mass spec: 382 (M−H).

Comparative Example 6

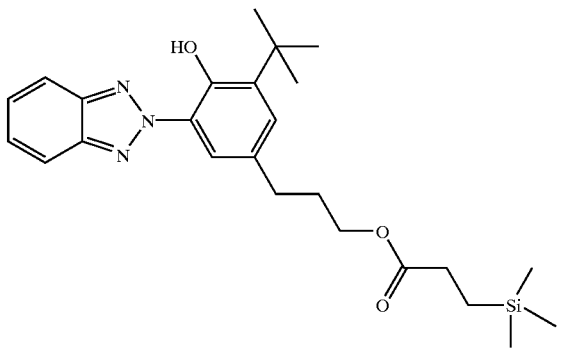

Following the procedure of Comparative Example 5, with appropriate starting materials, this compound is prepared as a light yellow solid;

mp 35–44° C.

$^{29}$Si NMR (500 MHz, CDCl$_3$, Cr(AcAc)$_2$): 2.50 ppm.

$^1$H NMR (500 MHz, CDCl$_3$): δ 11.20 (s, 1H), 8.20 (d, 1H), 7.94 (m, 2H), 7.48 (m, 2H), 7.19 (d, 1H), 4.20 (t, 2H), 2.78 (t, 2H), 2.35 (m, 2H), 2.05 (m, 2H), 1.55 (s, 9H), 0.91 (t, 2H), 0.10 (s, 9H).

Mass spec: 452 (M−H).

Comparative Example 7

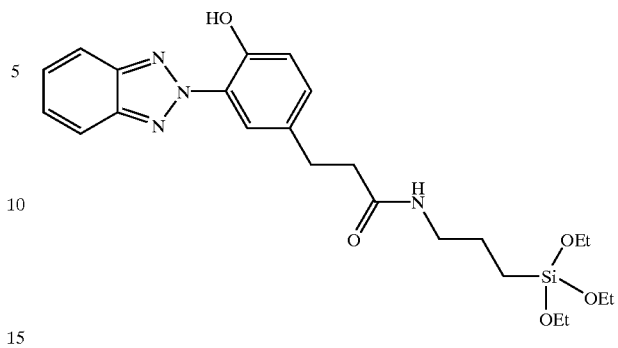

Following the procedure of instant Comparative Example 4, with appropriate starting materials, this compound is prepared as a white solid;

mp 128–138° C.

$^{29}$Si NMR (CDCl$_3$, 500 MHz, Cr(AcAc)$_2$): −45.44 ppm.

$^1$H NMR (CDCl$_3$, 500 MHz): δ 11.18 (s, 1H), 8.26 (d, 1H), 7.94 (m, 2H), 7.49 (m, 2H), 7.21 (dd, H), 7.12 (d, 1H), 5.72 (broad,$_1$H), 3.79 (q, 6H), 3.25 (q, 2H), 3.03 (t, 2H), 2.52 (t, 2H), 1.59 (quintet, 2H), 1.21 (t, 9H), 0.58 (t, 2H).

Mass spec: 897 (M−H).

EXAMPLE 107

5-Trifluoromethyl-2-[2-hydroxy-3-(3-triethoxysilyl)propyl-5-tert-octylphenyl]-2H-benzotriazole

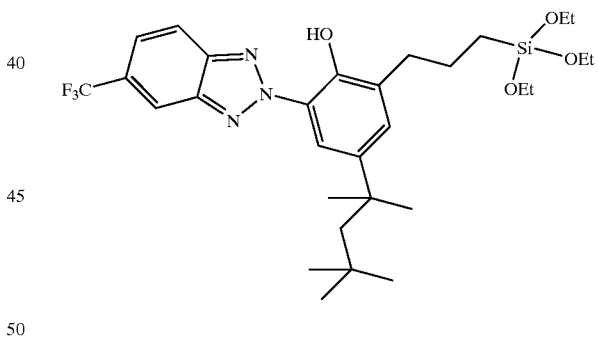

The title compound is prepared by the procedure of Example 3 of U.S. Pat. No. 5,391,795 using 5-trifluoromethyl-2-(2-hydroxy-3-allyl-5-tert-octylphenyl)-2H-benzotriazole prepared in Example 3 above, Karstedt's catalyst (complex of divinyltetramethyldisiloxane with platinum) and triethoxysilane. It is isolated as a viscous yellow oil.

$^{29}$Si NMR (CDCl$_3$, 500 MHz, Cr(AcAc)$_2$): −44.78 ppm.

$^1$H NMR (CDCl$_3$, 500 MHz): δ 11.50 (s, 1H), 8.32 (d, 1H), 8.27 (d, 1H), 8.09 (d, I H), 7.69 (dd, 1H), 7.31 (d, 1H), 3.83 (q, 6H), 2.83 (t, 2H), 1.84 (quintet, 2H), 1.80 (s, 2H), 1.45 (s, 6H), 1.22 (t, 9H), 0.78 (s, 9H), 0.76 (t, 2H).

$^{19}$F NMR (CDCl$_3$, 500 MHz, CF$_3$COOH): −68.88 ppm.

EXAMPLE 108

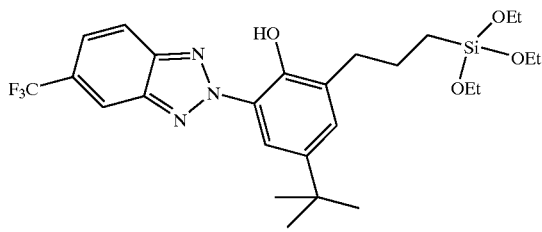

Following the procedure of instant Examples 3 and 4, with appropriate starting materials, this compound is prepared as a yellow viscous oil.
$^{29}$Si NMR (CDCl$_3$, 500 MHz, Cr(AcAc)$_2$): 44.7 ppm.
$^1$H NMR (CDCl$_3$, 500 MHz): δ 11.51 (s, 1H), 8.30 (d, 1H), 8.25 (d, 1H), 8.09 (d, 1H), 7.69 (dd, 1H), 7.31 (d, 1H), 3.81 (q, 6H), 2.83 (t, 2H), 1.85 (quintet, 2H), 1.25 (t, 9H), 0.78 (s, 9H), 0.76 (t, 2H).
$^{19}$F NMR (CDCl$_3$, 500 MHz, CF$_3$COOH): −68.8 ppm.

EXAMPLE 109

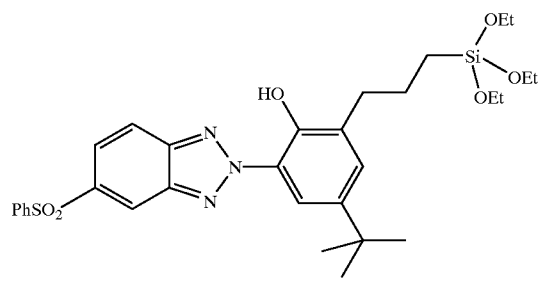

Following the procedures of instant Examples 3 and 4, with appropriate starting materials, this compound is prepared as a yellow viscous oil.
$^{29}$Si NMR (CDCl$_3$, 500 MHz, Cr(AcAc)$_2$): −44.82 ppm.
$^1$H NMR (CDCl$_3$, 500 MHz): δ 11.40 (s, 1H), 8.73 (d,1H), 8.25 (d, 1H), 8.03 (d, 1H), 8.00 (m, 2H), 7.91 (dd, 1H), 7.61–7.55 (m, 3H), 7.32 (d, 1H), 3.83 (q, 6H), 2.83 (t, 2H), 1.83 (quintet, 2H), 1.39 (s, 9H), 1.23 (t, 9H), 0.76 (t, 2H).

EXAMPLE 110

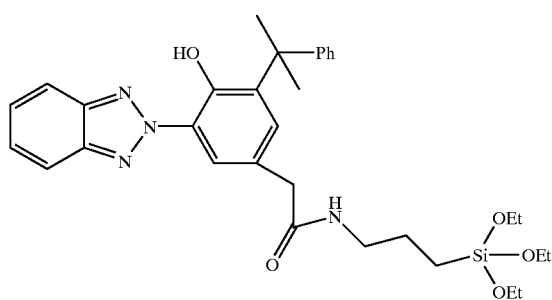

Following the procedure of instant Comparative Example 4, with appropriate starting materials, this compound is prepared as a light yellow solid;
mp 106–116° C.
$^{29}$Si NMR (CDCl$_3$, 500 MHz, Cr(AcAc)$_2$): −45.57 ppm.
$^1$H NMR (CDCl$_3$, 500 MHz): δ 11.56 (s, 1H), 8.28 (d, 1H), 7,84 (m, 2H), 7.49 (d, 1H), 7.45 (m, 2H), 7.28–7.18 (m, 5H), 5.76 (broad, 1H), 3.77 (q, 6H), 3.68 (s, 2H), 3.30 (t, 2H), 1.62 (quintet, 2H), 1.18 (t, 9H), 0.61 (t, 2H).

Mass spec: 589 (M−H).

EXAMPLE 111

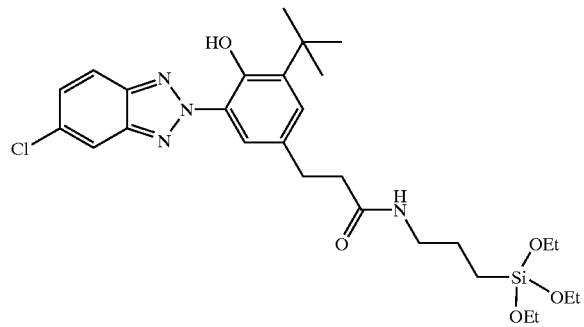

Following the procedure of instant Comparative Example 4, with appropriate starting materials, this compound is prepared as a light yellow solid;

mp 138–141° C.
$^{29}$Si NMR (CDCl$_3$, 500 MHz, Cr(AcAc)$_2$): −45.46 ppm.
$^1$H NMR (CDCl$_3$, 500 MHz): δ 11.56 (s, 1H), 8.12 (d, 1H), 7.94 (d, 1H), 7.88 (d, 1H), 7.44 (dd, 1H), 7.24 (d, 1H), 5.72 (broad, 1H), 3.80 (q, 6H), 3.27 (t, 2H), 3.02 (t, 2H), 2.52 (t, 2H), 1.62 (quartet, 2H), 1.50 (s, 9H), 1.22 (t, 9H), 0.61 (t, 2H).

Mass spec: 575 (M−H).

EXAMPLE 112

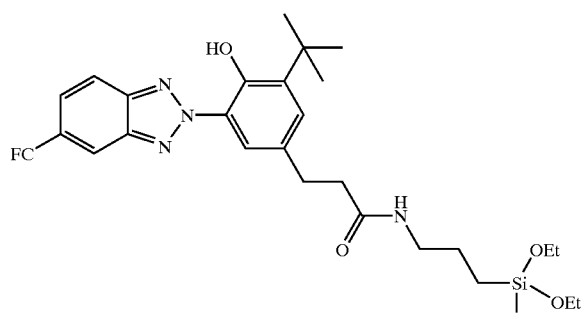

Following the procedure of instant Comparative Example 4, with appropriate starting materials, this compound is prepared as a light yellow solid;

mp 143–146° C.
$^{29}$Si NMR (CDCl$_3$, 500 MHz, Cr(AcAc)$_2$): −45.5 ppm.
$^1$H NMR (CDCl$_3$, 500 MHz): δ 11.53 (s, 1H), 8.29 (d, 1H), 8.16 (d, 1H), 8.06 (d, 1H), 7.68 (dd, 1H), 7.27 (d,1H), 5.76 (broad,1H), 3.80 (q, 6H), 3.27 (q, 2H), 3.03 (t, 2H), 2.53 (t, 2H), 1.62 (quintet, 2H), 1.50 (s, 9H), 1.21 (t, 9H), 0.61 (t, 2H).
$^{19}$F NMR (CDCl$_3$, 500 MHz, CF$_3$COOH): −68.9 ppm.

Mass spec: M/Z=610.

EXAMPLE 113

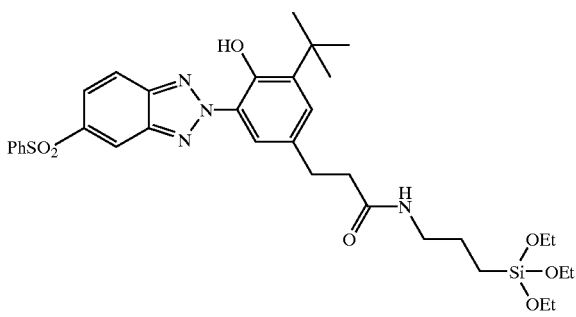

Following the procedure of instant Comparative Example 4, with appropriate starting materials, this compound is prepared as a yellow solid;
mp 123–130° C.
$^{29}$Si NMR (CDCl$_3$, 500 MHz, Cr(AcAc)$_2$): −45.45 ppm.
$^1$H NMR (CDCl$_3$, 500 MHz): δ 11.43 (s, 1H), 8.71 (d, 1H), 8.13 (d, 1H), 8.03 (d, 3H), 7.90 (dd, 1H), 7.61 (t, 1H), 7.55 (t, 2H), 5.76 (broad, 1H), 3.80 (q, 2H), 3.20 (q, 2H), 3.01 (t, 2H), 2.51 (t, 2H), 1.61 (quintet, 2H), 1.48 (s, 9H), 1.20 (t, 9H) 0.60 (t, 2H).
Mass spec: 681 (M−H).

EXAMPLE 114

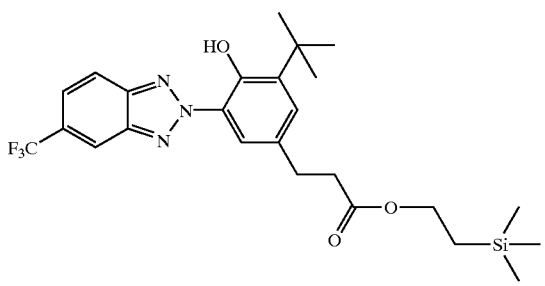

Following the procedure of Comparative Example 5, with appropriate starting materials, this compound is prepared as a light yellow solid;
mp: 55–61° C.
$^{29}$Si NMR (CDCl$_3$, 500 MHz, Cr(AcAc)$_2$): 0.21 ppm.
$^1$H NMR (CDCl$_3$, 500 MHz): δ 11.56 (s, 1H), 8.36 (d, 1H), 8.21 (d, 1H), 8.11 (d, 1H), 7.71 (d, I H), 7.27 (d, 1H), 4.24 (q, 2H), 3.01 (t, 2H), 2.69 (t, 2H), 1.55 (s, 9H), 1.01 (t, 2H), 0.15 (s, 9H).
Mass spec: 506 (M−H)

EXAMPLE 115

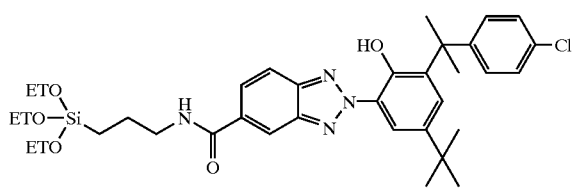

Following the procedure of Comparative Example 4, with appropriate starting materials, this compound is prepared as a yellow viscous oil.
$^1$H NMR (CDCl$_3$, 500 MHz): δ 11.15 (s, 1H), 8.40 (d, 1H), 8.35 (d, 1H), 7.91 (d, 1H), 7.62 (d, 1H), 7.36 (d, 1H), 7.30–7.15 (m, 4H), 6.65 (broad, 1H), 3.85 (q, 6H), 3.50 (t, 2H), 1.80 (s, 6H), 1.65 (m, 2H), 1.55 (s, 9H), 1.25 (t, 9H), 0.63 (t, 2H).

Application Example 1

Automotive Coatings Compositions

To ascertain the effect on thermal durability and loss rate from a high solids thermoset acrylic coating composition containing an instant benzotriazole UV absorber, the following tests are carried out.

A high solids thermoset acrylic clear coat is prepared by mixing an experimental acrylic polyol resin and hexamethoxymethylmelamine (Resimene® 747, Monsanto) at a solids ratio of 60/40. The dodecylbenzene sulfonic acid catalyst (Nacure® 5225; King Industries) is added at 0.70% by weight. A flow aid Modaflow® (Monsanto) is added at 0.25% by weight to form a model acrylic melamine resin system.

The model clear coat is reduced with xylene to a viscosity of 26–27 second using a Zahn #2 cup and applied via a conventional air spray at 50 psi (3.5 Kg/cm$^2$) over a 1″×3″ (2.54×7.62 cm) quartz slide. Cure is achieved by baking the slide for 30 minutes at 260° F. (127° C.). The clear coat is stabilized with 1% by weight of a hindered amine light stabilizer bis-(1-octyloxy-2,2,6,6-tetramethylpiperidin-4-yl) sebacate, Tinuvin® 123 (Ciba). The various test UV absorbers are incorporated at about 5 mmol % by weight in the clear coat. The film thickness on the quartz slides range from 1.15 to 1.41 mils (0.029 to 0.036 mm).

The films on the quartz slides are weathered according to the following conditions in Xenon Arc Weather-Ometer with a controlled irradiance at 6500 W, using inner quartz and outer borosilicate S-type filter. The irradiation cycle is as follows: 40 minutes of straight irradiation with no water spray, followed by 20 minutes of light plus front spray, followed by 60 minutes of light irradiation and finally by 60 minutes dart plus rear spray (condensation). The setting is at 0.55 W/m$^2$ at 340 nm, 1.98 kJ/hour. In the light cycle the black panel temperature is controlled at 70±2° C. The relative humidity in the light cycle is in the range of 50–55% and in the dark cycle 100%. The absorbance of the long wavelength UV band as a function of Xenon arc weathering hours are recorded.

To follow the loss of UV absorbers from the clear coats, UV spectra are measured initially and after weathering at regular intervals. The UV spectrophotometer measures absorbance linearly up to 5.5 absorbance units using a reference beam attenuation technique.

It is assumed that the degradation products from the UV absorber do not contribute to the UV spectrum. This is tested by following the ratio of absorbance of the band at about 300 nm and the band at about 340 nm. The ratio does not change upon weathering the sample. This suggests that the UV spectrum of the weathered films correspond to the amount of W absorber remaining in the film with very little if any contribution to the spectrum by photodegradants.

Representative test compounds are incorporated into a high solid thermoset acrylic melamine resin at a concentration of 3% by weight to give equal molar concentrations of the test UV absorber in equal film thickness. The test samples are exposed for 1461 hours respectively.

| Compound | Units of Absorbance Initial | Units of Absorbance Final | Units of Absorbance Loss |
|---|---|---|---|
| Uvinul ® 3049 (1.86%) | 2.26 | 0 | 2.26 |
| Comparative Ex. 1 (2.95%) | 6.38 | 0 | 6.38 |
| Tinuvin ® 928 (3.0%) | 1.98 | 1.62 | 0.36 |

Tinuvin ® 928 is 2-(2-hydroxy-3-α-cumyl-5-t-octylphenyl)-2H-benzotriazole (Ciba).
Uvinul ® 3049 is 4,4'dimethoxy-2,2'-dihydroxybenzophenone (BASF).
This Example displays the general superiority of hydroxyphenylbenzotriazole UV absorbers that contain alpha cumyl groups vs. benzophenone UV absorbers.

Application Example 2

UV Absorption Example

The benzotriazoles differ by their substitution in the 5-position of the benzo ring. The UV absorption spectra are measured in ethyl acetate at approximately 20 mg/L concentration. The instant compounds are clearly red-shifted as compared to the compound having only hydrogen at the benzo ring 5 position.

| Compound | λmax (nm) | absorbance at 375 nm |
|---|---|---|
| Comparative Ex. 5 | 338 | 0.09 |
| Comparative Ex. 6 | 342 | 0.20 |
| Instant Ex. 114 | 351 | 0.32 |

Application Example 3

UV Absorption Spectra

The UV absorption spectra are measured in ethyl acetate at approximately 20 mg/L concentration. The instant compounds are clearly red-shifted as compared to the compounds disclosed in U.S. Pat. No. 5,391,795.

| Compound | λmax (nm) | absorbance at 375 nm |
|---|---|---|
| Comparative Ex. 1 | 329 | 0.02 |
| Comparative Ex. 2 | 284 | 0.03 |
| Comparative Ex. 3 | 285 | 0.01 |
| Instant Ex. 107 | 349 | 0.36 |
| Instant Ex. 109 | 347 | 0.28 |

Application Example 4

UV Absorption Example

The benzotriazoles differ by their substitution in the 5-position of the benzo ring. The UV absorption spectra are measured in ethyl acetate at approximately 20 mg/L concentration. The instant compounds are clearly red-shifted as compared to the compound having only hydrogen at the benzo ring 5 position.

| Compound | λmax (nm) | absorbance at 375 nm |
|---|---|---|
| Comparative Ex. 7 | 341 | 0.08 |
| Comparative Ex. 4 | 343 | 0.15 |
| Instant Ex. 111 | 349 | 0.36 |
| Instant Ex. 112 | 351 | 0.29 |
| Instant Ex. 113 | 360 | 0.46 |
| Instant Ex. 115 | 350 | 0.23 |

In the following Examples the commercial benzotraizole UVA's are Tinuvin® 384, isooctyl 3-(2H-benzotriazol-2-yl) 5-tert-butyl-4-hydroxhydrocinnamate (Ciba)

Application Example 5

Thermal Permanence in Polymeric Coatings

Silicone coatings are prepared with methyl trimethoxy silane and 2.5% by weight of the additives of the table below. The aqueous acidic coating compositions are applied by spin-coating to 1.5" diameter quartz discs under conditions which result in a dry film thickness of 2 microns. All discs are allowed to flash at room temperature for 20–30 minutes, then one set of discs is baked at 125° C. for 60 minutes while another set is allowed to dry at room temperature at least overnight.

Thermal permanence of the test compounds is determined by using Beer's Law equation relating absorbance directly to concentration. It is assumed that in the ambient cured coating, all UVA is retained, and has not volatilized. Therefore, the amount of a compound lost by volatilization under these baking conditions is determined either by comparison of the absorbance from the ambient cured and oven cured coating applied at the same film thickness in the case of reactable UV absorbers or by extraction of non-reactable UV absorbers and comparison of the amount of UV absorber extracted from the ambient-cured and oven cured samples. Results are below.

| Compound | Percent UVA Lost |
|---|---|
| Tinuvin ® 384 | 5.6% |
| Present Example 112 | negligible |

It is seen that the reactable compounds of the present invention are retained to a significantly high degree.

Application Example 6

Absorbance Wavelength Coverage in Polysiloxanes

Coatings are prepared and coated on quartz discs as in applications Example 5. After oven cure at 125° C. for 60 minutes, absorbance scans are run from 250 nm to 450 nm. If two absorbance peaks are present, the peak at longer wavelength is recorded in location (nm). Long wavelength spectra coverage is also recorded by obtaining absorbance values at 375 nm. Results are below.

| Compound | Peak Absorbance Wavelength (nm) | Absorbance at 375 nm |
| --- | --- | --- |
| Comparative Example 3 | 287 (nm) | 0.013 |
| Comparative Example 4 | 343 (nm) | 0.155 |
| Present Example 112 | 353 (nm) | 0.216 |

It can be seen that the compounds of the present invention give a significantly broader spectral coverage than the benzoyl resorcinol compounds.

Application Example 7

Reactability

Coatings are prepared and coated on glass plates as in application Example 5. After ambient cure for 1 day, the coatings are removed from the glass substrate. Approximately 5 mg of the coating are weighed into a 10 ml volumetric flask, which is filled to mark with tetrahydrofuran (THF). After sonication for 60 minutes, the solution is filtered, then diluted to a known volume with THF. The amount of UVA extracted is determined by comparing the absorbance of the THF solution with absorbance of known standards. The percent reacted into the coating is calculated from the difference between the amount of UVA remaining in the coating after bake and the amount extracted. Results are found below.

| Compound | Percent Extracted |
| --- | --- |
| Tinuvin ® 384 | 89% |
| Tinuvin ® 928 | 97% |
| Comparative Example 4 | 5.0% |
| Instant Example 112 | 4.6% |

It is seen that the compounds of the present invention are successfully reacted into the coating.

Application Example 8

Color

Coatings are prepared and coated on quartz discs as in application Example 5. After ambient cure for 1 week, CILAB L*,a*,b* values are obtained using a MacBeth Coloreye spectrophotometer. D65 illuminant, observer angle 10° with specular component included are used. Color readings are obtained on coated discs in reflectance mode with white tile standard as backing. Results are found below.

| Compound | YI |
| --- | --- |
| Comparative Example 3 | 2.14 |
| Instant Example 112 | 2.07 |

Coatings prepared with additives of the present invention are clear, have no haze, and have good color.

Application Example 9

Silicone Coatings over Solid Substrate

Additives according to the present invention are incorporated into a silica resin solution according to application Example 5, yielding a silicone hardcoat solution with 5% by weight silylated ultraviolet absorbing agent based on solids. The solution is applied to a glass slide. Subsequent to solvent evaporation and baking at 100° C. for 1 hour, an optically clear silicone hardcoat is formed on the glass. The coatings are exposed to UV light by passing them five times under two 300 watt/inch medium pressure mercury lamps using a conveyor moving at about 25 ft/min.

The silicone hardcoats prepared containing silylated additives of the present invention, in particular compounds of Examples 107–115, exhibit excellent resistance to abrasion (Taber abrasion test); and microcracking resistance and low haze upon UV exposure.

The samples are also exposed in an Atlas Ci35a WeatherOmeter at 0.77 W/m$^2$ irradiance at 340 nm with Type S borosilicate inner and outer filters. The lamp runs in a cycle of 160 minutes light at 45° C. dry bulb temperature and 50% relative humidity (ca. 65° C. black panel temperature) and 20 minutes dark. The last 15 minutes of the dark cycle is with a front and back side water spray. Under these conditions, the samples accumulate 2700 kJ/m$^2$ at 340 nm in 1100 hours of exposure. This is approximately equivalent to one year Florida exposure. The samples are mounted on the standard sample holders with spring clips.

The silicone hardcoats prepared containing silylated additives of the present invention, in particular compounds of Examples 107–115, exhibit excellent microcracking resistance and low haze upon UV exposure in a WeatherOmeter.

Application Example 10

Silicone Coatings over Polycarbonate

Bisphenol-A based polycarbonate panels are primed with polymethylmethacrylate and are flow coated with a silicone hardcoat prepared according to application Example 9. The coated samples are baked for 90 minutes at 100° C. yielding polycarbonate coatings with an optically clear 5 micron silicone hardcoat. The silicone hardcoats prepared containing silylated additives of the present invention, in particular compounds of Examples 107–115, exhibit excellent resistance to abrasion (Taber abrasion test); and microcracking resistance and low haze upon UV exposure. The present compositions also perform especially well in WeaterOmeter exposure as in application Example 9.

Application Example 11

Colloidal Silicone Coatings 0.5 g of the present silylated additives are added to 50 g of silica resin (condensed methyl trimethoxy silane/aqueous colloidal silica resin at approximately 20% solids in an alcohol solvent) to produce a mixture. The mixture is stirred overnight and passed through a 0.30 micron filter yielding a silicone hardcoat solution with 5 pph silylated ultraviolet absorbing agent based on solids. The solution is applied to both glass slides and polycarbonate panels as above.

The silicone hardcoats prepared containing silylated additives of the present invention, in particular compounds of Examples 107–115, exhibit excellent resistance to abrasion (Taber abrasion test); and microcracking resistance and low haze upon UV exposure. The present compositions also perform especially well in WeaterOmeter exposure as in application Example 9.

The silylated additives of the present invention may crosslinked or reacted into any type of commercially available siloxane automotive clear coats, for example coatings as described in U.S. Pat. Nos. 5,932,667, 5,182,174 and 6,080,816, the relevant disclosures of which are hereby incorporated by reference. The present additives likewise may be crosslinked or reacted into siloxane coatings as described in U.S. Pat. Nos. 4,373,061, 5,391,795, 5,679,820, the relevant disclosures of which are also hereby incorporated by reference.

What is claimed is:

1. A compound of formula (I) or (II)

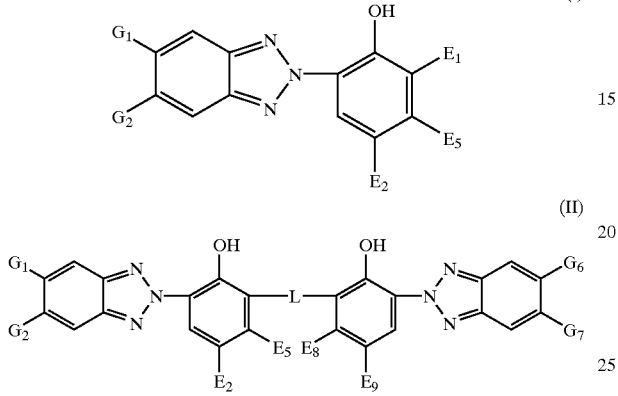

wherein $G_1$ and $G_6$ are independently hydrogen or halogen;

$G_2$ and $G_7$ are independently cyano, perfluoroalkyl of 1 to 12 carbon atoms, fluoro, chloro, —CO—$G_3$, —COO$G_3$, —CONH$G_3$, —CON($G_3$)$_2$, $E_3$SO$_2$—, $E_3$SO$_2$—, —PO(C$_6$H$_5$)$_2$,

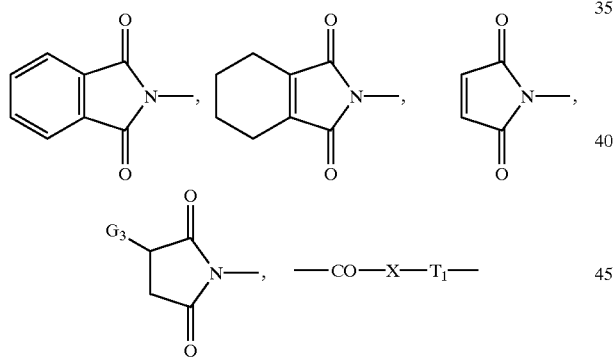

NH—$T_2$—Si(OR$_2$)$_n$(R$_1$)$_{3-n}$ or —CO—X—$T_1$—Si(OR$_2$)$_n$(R$_1$)$_{3-n}$;

or $G_7$ is also hydrogen;

or $G_2$ may also be hydrogen when $E_1$ is a group of formula (IV) or (V);

$T_1$ and $T_2$ are independently alkylene of 1 to 18 carbon atoms or alkylene-phenylene-alkylene of 8 to 20 carbon atoms;

$R_1$ and $R_2$ are independently alkyl of 1 to 18 carbon atoms, cycloalkyl of 5 to 12 carbon atoms, aryl of 6 to 10 carbon atoms or phenylalkyl of 7 to 20 carbon atoms;

n is 0, 1, 2 or 3;

X is —O—, —NE$_4$— or —NH—;

$G_3$ is hydrogen, straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;

$E_1$ is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms or by one or more of the following groups —$T_1$—Si(OR$_2$)$_n$(R$_1$)$_{3-n}$, —$T_1$—X—CO—X—$T_2$—Si(OR$_2$)$_n$(R$_1$)$_{3-n}$, —$T_1$—CO—X—$T_2$—Si(OR$_2$)$_n$(R$_1$)$_{3-n}$, —X—$T_1$—Si(OR$_2$)$_n$(R$_1$)$_{3-n}$, or —X—$T_2$—X—CO—X—$T_2$—Si(OR$_2$)$_n$(R$_1$)$_{3-n}$; or $E_1$ is alkyl of 1 to 24 carbon atoms substituted by one or two hydroxy groups;

or $E_1$ is a group of formula (IV) or (V)

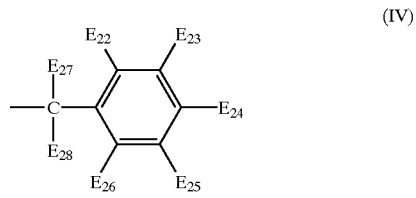

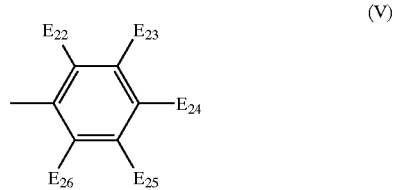

where $E_{27}$ and $E_{28}$ are independently alkyl of 1 to 18 carbon atoms, or cycloalkyl of 5 to 12 carbon atoms;

$E_{22}$, $E_{23}$, $E_{24}$, $E_{25}$ and $E_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOE$_{11}$, —OE$_4$, —NCO, —NHCOE$_{11}$, or —NE$_7$E$_8$, or mixtures thereof, where $E_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof; or $E_{22}$, $E_{23}$, $E_{24}$, $E_{25}$ and $E_{26}$ are independently phenyl, —OH, —OCOE$_{11}$, —OE$_{29}$, —NCO, —NHCOE$_{11}$ or —NE$_7$E$_8$, cyano, nitro, perfluoroalkyl of 1 to 12 carbon atoms, —COG$_3$, —COOG$_3$, —CON(G$_3$)$_2$, —CONHG$_3$, E$_3$S—, E$_3$SO—, E$_3$SO$_2$—, —P(O)(C$_6$H$_5$)$_2$, —P(O)(C$_3$)$_2$, —SO$_2$—X$_1$—E$_{29}$;

$X_1$ is —O—, —NH— or —NE$_4$—;

$E_{29}$ is straight or branched chain alkyl of 1 to 24 carbon atoms, straight or branched chain alkenyl of 2 to 18 carbon atoms, said alkyl or said alkenyl substituted by one or more —OH, —OCOE$_{11}$, —OE$_4$, —NCO, —NHCOE$_{11}$, —NE$_7$E$_8$, phthalimido,

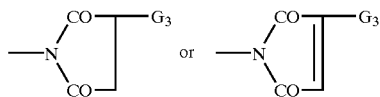

or mixtures thereof, where $E_4$ is straight or branched chain alkyl of 1 to 24 carbon atoms or alkenyl of 2 to 18 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$, or mixtures thereof; or $E_{29}$ is phenyl or phenylalkyl of 7 to 15 carbon atoms, or said phenyl or said phenylalkyl substituted by one to three alkyl groups of 1 to 4 carbon atoms;

$E_2$ and $E_9$ are independently hydrogen, straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by one to three alkyl of 1 to 4 carbon atoms or by one or more of the following groups —T$_1$—Si(OR$_2$)$_n$(R$_1$)$_{3-n}$, —T$_1$—X—CO—X—T$_2$—Si(OR$_2$)$_n$(R$_1$)$_{3-n}$, —T$_1$—CO—X—T$_2$—Si(OR$_2$)$_n$(R$_1$)$_{3-n}$, —X—T$_1$—Si(OR$_2$)$_n$(R$_1$)$_{3-n}$, or —X—T$_1$—X—CO—X—T$_2$—Si(OR$_2$)$_n$(R$_1$)$_{3-n}$; or $E_2$ and $E_9$ are independently said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where $E_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof; or $E_1$, $E_2$ and $E_9$ are also independently —T$_1$—Si(OR$_2$)$_n$(R$_1$)$_{3-n}$, —T$_1$—X—CO—X—T$_2$—Si(OR$_2$)$_n$(R$_1$)$_{3-n}$ or —T$_1$—CO—X—T$_2$—Si(OR$_2$)$_n$(R$_1$)$_{3-n}$;

$E_{11}$ is hydrogen, straight or branched chain alkyl of 1 to 18 carbon atoms, straight or branched chain alkenyl of 2 to 18 carbon atoms, cycloalkyl of 5 to 12 carbon atoms, aryl of 6 to 14 carbon atoms or phenylalkyl of 7 to 15 carbon atoms;

L is alkylene of 1 to 12 carbon atoms, alkylidene of 2 to 12 carbon atoms, benzylidene, p-xylylene, cycloalkylidene of 5 to 12 carbon atoms or α,α,α',α'-tetramethyl-m-xylylene;

$E_3$ is alkyl of 1 to 20 carbon atoms, said alkyl substituted by alkoxycarbonyl of 2 to 9 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, $E_5$ and $E_8$ are independently the same as $E_2$; or $E_5$ and $E_8$ are independently hydrogen, —X—E$_1$, —X—CO—E$_2$, —X—CO—X$_1$, —X—T$_1$—Si(OR$_2$)$_n$(R$_1$)$_{3-n}$, or —X—T$_1$—X—CO—X—T$_2$—Si(OR$_2$)$_n$(R$_1$)$_{3-n}$;

$X_1$ is —NH—E$_4$ or —X—E$_2$;

with the proviso that at least one of $G_2$, $E_1$, $E_2$ and $E_5$ contains a group —T$_1$—Si(OR$_2$)$_n$(R$_1$)$_{3-n}$, —T$_1$—X—CO—X—T$_2$—Si(OR$_2$)$_n$(R$_1$)$_{3-n}$ or —T$_1$—CO—X—T$_2$—Si(OR$_2$)$_n$(R$_1$)$_{3-n}$; where $T_1$ and $T_2$ are independently alkylene of 1 to 18 carbon atoms or alkylene-phenylene-alkylene of 8 to 20 carbon atoms, and $R_1$ and $R_2$ are independently alkyl of 1 to 18 carbon atoms, cycloalkyl of 5 to 12 carbon atoms, aryl of 6 to 10 carbon atoms or phenylalkyl of 7 to 20 carbon atoms, and n is 0, 1, 2 or 3 and with the proviso that when $G_1$ is hydrogen and $G_2$ is chloro, fluoro or —COOG$_3$, $E_1$ is a group of formula (IV) or (V).

2. A compound according to claim 1 of formula IA or IIA

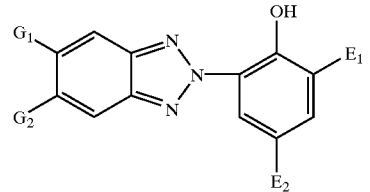

(IA)

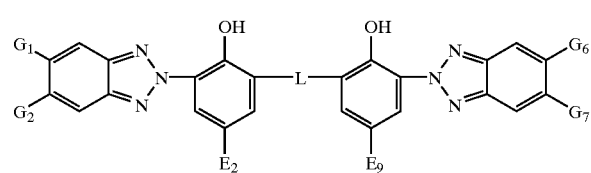

(IIA)

wherein $G_1$ and $G_6$ are hydrogen, $G_2$ and $G_7$ are independently cyano, CF$_3$—, fluoro, —CO—G$_3$ or $E_3$SO$_2$—, or $G_7$ is also hydrogen, $G_3$ is straight or branched chain alkyl of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms, $E_1$ is phenylalkyl of 7 to 15 carbon atoms, phenyl, or said phenyl or said phenylalkyl substituted on the phenyl ring by 1 to 4 alkyl of 1 to 4 carbon atoms, $E_2$ and $E_9$ are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or $E_2$ is said alkyl of 1 to 24 carbon atoms or said alkenyl of 2 to 18 carbon atoms substituted by one or more —OH, —OCOE$_{11}$, —OE$_4$, —NCO, —NH$_2$, —NHCOE$_{11}$, —NHE$_4$ or —N(E$_4$)$_2$, or mixtures thereof, where $E_4$ is straight or branched chain alkyl of 1 to 24 carbon atoms; or said alkyl or said alkenyl interrupted by one or more —O—, —NH— or —NE$_4$— groups or mixtures thereof and which can be unsubstituted or substituted by one or more —OH, —OE$_4$ or —NH$_2$ groups or mixtures thereof;

$E_{11}$ is hydrogen, straight or branched chain alkyl of 1 to 18 carbon atoms, straight or branched chain alkenyl of 2 to 18 carbon atoms, cycloalkyl of 5 to 12 carbon atoms, aryl of 6 to 14 carbon atoms or phenylalkyl of 7 to 15 carbon atoms;

$E_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms;

L is methylene;

with the proviso that at least one of $E_1$, $E_2$ and $E_9$ contains a group $—T_1—Si(OR_2)_n(R_1)_{3-n}$, $—T_1—X—CO—X—T_2—Si(OR_2)_n(R_1)_{3-n}$, $—T_1—CO—X—T_2—Si(OR_2)_n(R_1)_{3-n}$, $—X—T_1—Si(OR_2)_n(R_1)_{3-n}$ or $—X—T_1—X—CO—X—T_2—Si(OR_2)_n(R_1)_{3-n}$;

where $T_1$ and $T_2$ are independently alkylene of 2 or 3 carbon atoms, and $R_1$ and $R_2$ are independently alkyl of 1 to 6 carbon atoms or phenyl, and n is 0, 1, 2 or 3.

3. A compound according to claim 1 of formula IA compound of formula IA

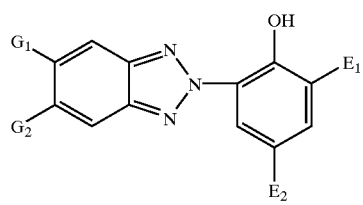

(IA)

wherein $G_1$ is hydrogen, $G_2$ is $CF_3—$ or $E_3SO_2—$, $E_1$ is hydrogen or straight or branched alkyl of 2 to 24 carbon atoms, $E_2$ is as defined above, and $E_3$ is straight or branched chain alkyl of 1 to 7 carbon atoms, with the proviso that $E_2$ contains a group $—T_1—Si(OR_2)_n(R_1)_{3-n}$, $—T_1—X—CO—X—T_2—Si(OR_2)_n(R_1)_{3-n}$, $—T_1—CO—X—T_2—Si(OR_2)_n(R_1)_{3-n}$, $—X—T_1—Si(OR_2)_n(R_1)_{3-n}$ or $—X—T_1—X—CO—X—T_2—Si(OR_2)_n(R_1)_{3-n}$; where $T_1$ and $T_2$ are independently alkylene of 2 or 3 carbon atoms, and $R_1$ and $R_2$ are independently alkyl of 1 to 6 carbon atoms or phenyl, and n is 0, 1, 2 or 3.

4. A compound according to claim 1 wherein $T_1$ and $T_2$ are independently alkylene of 2 or 3 carbon atoms.

5. A compound according to claim 1 wherein $R_1$ and $R_2$ are independently alkyl of 1 to 6 carbon atoms or phenyl.

6. A compound of formula I according to claim 1 which is (a) 5-trifluoromethyl-2-[2-hydroxy-3-(3-triethoxysilyl)propyl-5-tert-octylphenyl]-2H-benzotriazole;

(b) 5-trifluoromethyl-2-{2-hydroxy-3-tert-butyl-5-[3-(3-triethyoxysilyl)propylcarbamoyloxy)-propyl]phenyl}2H-benzotriazole;

(c) 5-trifluoromethyl-2-{2-hydroxy-3-tert-butyl-5-[2-(3-triethyoxysilyl)propylcarbamoyl-oxy)ethyl]phenyl}2H-benzotriazole;

(d) 5-trifluoromethyl-2-{2-hydroxy-5-[2-(3-triethyoxysilyl)propyl-carbamoyloxy)ethyl]-phenyl}2H-benzotriazole;

(e) 5-trifluoromethyl-2-{2-hydroxy-3-α-cumyl-5-[2-(3-triethyoxysilyl)propylcarbamoyl-oxy)ethyl]phenyl}-2H-benzotriazole;

(f) 5-trifluoromethyl-2-{2-hydroxy-3-tert-butyl-5-[2-(3-(diethoxymethylsilyl)propylamino-carbonylethyl]phenyl}2H-benzotriazole;

(g) 5-phenylsulfonyl-2-{2-hydroxy-3-tert-butyl-5-[3-(2-ethoxydimethylsilyl)ethylcarbonyl-oxy)propyl]phenyl}2H-benzotriazole;

(h) 5-n-butylsulfonyl-2-{2-hydroxy-3-tert-butyl-5-[2-(3-ethoxydimethylsilyl)propyl-oxycarbonyl)ethyl]phenyl}2H-benzotriazole;

(i) 5-trifluoromethyl-2-[2-hydroxy-3-(ethoxydimethylsilyl)propyl-5-tert-octylphenyl]-2H-benzotriazole;

(j) 5-trifluoromethyl-2-[2-hydroxy-3-(trimethylsilyl)propyl-5-tert-butylphenyl]-2H-benzotriazole;

(k) 5-[3-(diethoxyethylsilyl)propoxycarbonyl]-2-(2-hydroxy-3-α-cumyl-5-tert-octyl-phenyl)-2H-benzotriazole;

(l) 5-[3-(diethoxyethylsilyl)propylaminocarbonyl]-2-(2-hydroxy-3-α-cumyl-5-tert-octyl-phenyl)-2H-benzotriazole;

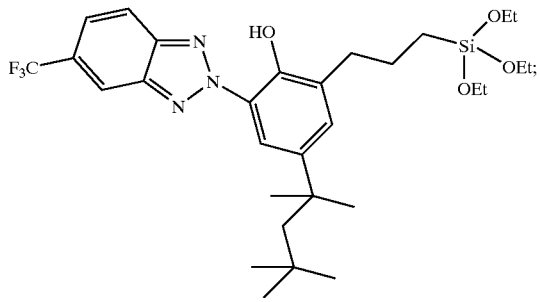

(m)

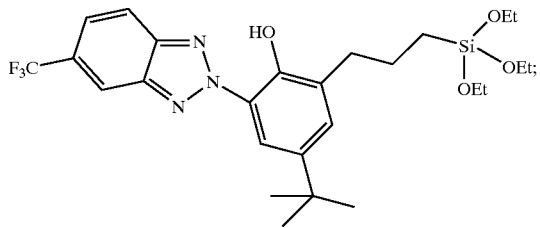

(n)

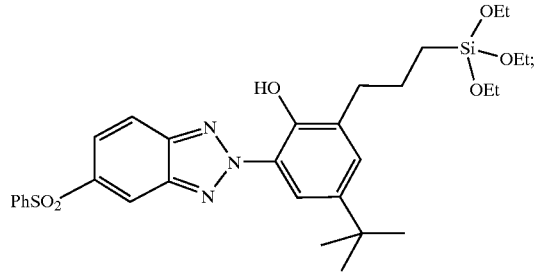

(o)

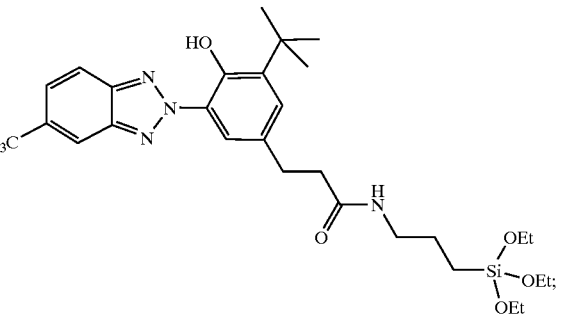

(r)

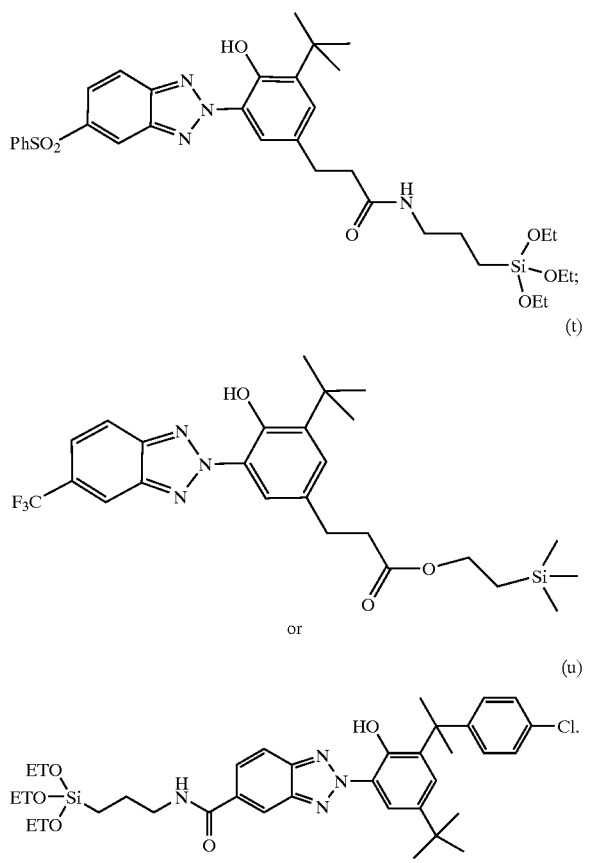

7. A composition stabilized against light-induced degradation which comprises
(a) an organic material subject to light-induced degradation, and
(b) an effective stabilizing amount of a compound of formula (I) or (II) according to claim 1.

8. A composition according to claim 7 wherein component (a) is a natural, semi-synthetic or synthetic polymer.

9. A composition according to claim 8 wherein the polymer is a thermoplastic polymer.

10. A composition according to claim 7 wherein the polymer is a polyolefin or polycarbonate.

11. A composition according to claim 10 wherein the polymer is polyethylene or polypropylene.

12. A composition according to claim 7 wherein the polymer is polypropylene; or the polymer is a styrenic, ABS, a nylon, a polyester such as poly(ethylene terephthalate) or poly(butylene terephthalate), a polyurethane, an acrylate, a rubber modified styrenic, poly(vinyl chloride), poly(vinyl butyral), polyacetal (polyoxymethylene), poly(ethylene naphthalene-dicarboxylate), or other blends or copolymers such as poly(ethylene/1,4-cyclohexylenedimethylene terephthalate) PETG or an ionomer.

13. A composition according to claim 8 wherein the polymer is a siloxane coating as a screening layer over polycarbonate.

14. A composition according to claim 7 wherein the organic material of component (a) is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

15. A composition according to claim 7 wherein the organic material of component (a) is a acrylosilane coating useful in organosilicone hardcoats or softcoats for automotive applications such as GENIVA (DuPont) coatings or for multilayered compositions.

16. A composition according to claim 7 which additionally contains as coadditive a phenolic antioxidant selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris-[2-(3,5-di-tert-butyl-4-hydroxyhydrocinnamoyloxy)ethyl]isocyanur ate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzyl-phosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-eth yl]-oxamide.

17. A composition according to claim 7 which additionally contains as coadditive a hindered amine selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dio ne, tris(2,2,6,6-tetramethylpiperidin-4-yl) nitrilotriacetate, 1,2-bis(2,2,6,6-tetramethyl-3-oxopiperazin4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N', N", N'''-tetrakis[(4,6-bis(butyl-1,2,2,6,6-pentamethylpiperidin-4-yl)-amino-s-triazin-2-y l]-1,10-diamino4,7-diazadecane, mixed [2,2,6,6-tetramethylpiperidin-4-yl/β,β,β',β'-tetramethyl-3,9-(2,4,8,10-tetraoxaspiro[5.5]-undecane) diethyl]1,2,3,4-butanetetracarboxylate, mixed [1,2,2,6,6-pentamethylpiperidin-4-yl/β,β,β',α'-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6, 6-pentamethylpiperidin-4-yl-n-dodecylsuccinimide, N-1-acetyl-2,2,6,6-tetramethylpiperidin-4-yl-n-dodecylsuccinimide, 1-acetyl-3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethyl-piperidin-4-yl) imino], 2,4,6-tris[N-(1-cyclohexyloxy-2,2,6,6-tetramethylpiperidin-4-yl)-n-butylamino]-s-triazine, and 1-(2-hydroxy-2-ethylpropoxy-4-octadecanoyloxy-2,2,6,6-tetramethylpiperidine.

18. A composition according to claim 7 which additionally contains as coadditive another UV absorber selected from the group consisting of the benzotriazoles, s-triazines, the oxanilides, the benzylidene malonates the hydroxybenzophenones, benzoates and α-cyanoacrylates.

19. A composition according to claim 18 wherein the UV absorber is a 2-hydroxyphenyl-2H-benzotriazole selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-tert-octylphenyl]-2H-benzotriazole;

2-{2-hydroxy-3-tert-butyl-5-[2-(omega-hydroxy-octa(ethyleneoxy)carbonyl)ethyl]phenyl}-2H-benzotriazole;

5-chloro-2-(2-hydroxy-3,5-di-tert-butylphenyl)-2H-benzotriazole;

5-chloro-2-(2-hydroxy-3-tert-butyl-5-methylphenyl)-2H-benzotriazole;

2-(2-hydroxy-5-tert-octylphenyl)-2H-benzotriazole;

2-{2-hydroxy-3-tert-butyl-5-[2-(octyloxy)carbonyl)ethyl]phenyl}-2H-benzotriazole;

5-trifluoromethyl-2-(2-hydroxy-3-α-cumyl-5-tert-octylphenyl)-2H-benzotriazole;

5-trifluoromethyl-2-(2-hydroxy-5-tert-octylphenyl)-2H-benzotriazole;

5-trifluoromethyl-2-(2-hydroxy-3,5-di-tert-octylphenyl)-2H-benzotriazole;

2,2'-methylene-bis[6-(5-trifluoromethyl-2H-benzotriazol-2-yl)-4-tert-octylphenol];

methylene-2-[4-tert-octyl-6-(2H-benzotriazol-2-yl)phenol]2'-[4-tert-octyl-6-(5-trifluoromethyl-2H-benzotriazol-2-yl)phenol];

3-(5-trifluoromethyl-2H-benzotriazol-2-yl)-5-tert-butyl-4-hydroxyhydrocinnamic acid;

methyl 3-(5-trifluoromethyl-2H-benzotriazol-2-yl)-5-tert-butyl-4-hydroxyhydrocinnamate;

isooctyl 3-(5-trifluoromethyl-2H-benzotriazol-2-yl)-5-tert-butyl-4-hydroxyhydrocinnamate;

5-trifluoromethyl-2-[2-hydroxy-5-(3-hydroxypropyl)phenyl]-2H-benzotriazole;

5-trifluoromethyl-2-[2-hydroxy-5-(3-acryloyloxypropyl)phenyl]-2H-benzotriazole;

5-trifluoromethyl-2-[2-hydroxy-5-(3-methacryloyloxypropyl)phenyl]-2H-benzotriazole;

5-trifluoromethyl-2-[2-hydroxy-5-(3-acrylyaminopropyl)phenyl]-2H-benzotriazole;

5-trifluoromethyl-2-[2-hydroxy-5-(3-methacrylylaminopropyl)phenyl]-2H-benzotriazole;

5-trifluoromethyl-2-(2-hydroxy-3-α-cumyl-5-tert-butylphenyl)-2H-benzotriazole;

5-trifluoromethyl-2-(2-hydroxy-3-α-cumyl-5-nonylphenyl)-2H-benzotriazole;

5-trifluoromethyl-2-[2-hydroxy-3-α-cumyl-5-(2-hydroxyethyl)phenyl]-2H-benzotriazole;

5-trifluoromethyl-2-[2-hydroxy-3-α-cumyl-5-(3-hydroxypropyl)phenyl]-2H-benzotriazole;

5-trifluoromethyl-2-(2-hydroxy-3,5-ditert-amylphenyl)-2H-benzotriazole;

5-trifluoromethyl-2-(2-hydroxy-3,5-ditert-butylphenyl)-2H-benzotriazole;

5-trifluoromethyl-2-(2-hydroxy-3-dodecyl-5-methylphenyl)-2H-benzotriazole;

5-Trifluoromethyl-2-[2-hydroxy-3-tert-butyl-5-(3-hydroxypropyl)phenyl]-2H-benzotriazole;

5-trifluoromethyl-2-[2-hydroxy-3-tert-butyl-5-(2-hydroxyethyl)phenyl]-2H-benzotriazole;

5-trifluoromethyl-2-[2-hydroxy-5-(2-hydroxyethyl)phenyl]-2H-benzotriazole;

5-trifluoromethyl-2-(2-hydroxy-3,5-di-α-cumylphenyl)-2H-benzotriazole;

5-fluoro-2-(2-hydroxy-3,5-di-α-cumylphenyl)-2H-benzotriazole;

5-butylsulfonyl-2-(2-hydroxy-3,5-di-α-cumylphenyl)-2H-benzotriazole;

5-butylsulfonyl-2-(2-hydroxy-3,5-di-tert-butylphenyl)-2H-benzotriazole; and 5-butylsulfonyl-2-(2-hydroxy-3,5-di-tert-octylphenyl)-2H-benzotriazole.

20. A composition according to claim 18 wherein the UV absorber is a tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine; and 2,4-bis(2,4-dimethylphenyl)-6-[2-hydroxy-4-(3-do-/tri-decyloxy-2-hydroxypropoxy)-phenyl]-s-triazine.

21. A composition stabilized against light-induced degradation which comprises an ultraviolet light screening layer over a solid substrate, wherein the screening layer comprises a silicone coating and at least one compound selected from the group consisting of compounds of formuae (I) and (II) according to claim 1.

22. A composition according to claim 21, in which the solid substrate is polycarbonate.

23. A composition according to claim 22, wherein the compounds of formulae (I) and (II) are selected from the group consisting of (a) 5-trifluoromethyl-2-[2-hydroxy-3-(3-triethoxysilyl)propyl-5-tert-octylphenyl]-2H-benzotriazole;

(b) 5-trifluoromethyl-2-{2-hydroxy-3-tert-butyl-5-[3-(3-triethyoxysilyl)propylcarbamoyloxy)-propyl]phenyl}2H-benzotriazole;

(c) 5-trifluoromethyl-2-{2-hydroxy-3-tert-butyl-5-[2-(3-triethyoxysilyl)propylcarbamoyl-oxy)ethyl]phenyl}-2H-benzotriazole;

(d) 5-trifluoromethyl-2-{2-hydroxy-5-[2-(3-triethyoxysilyl)propyl-carbamoyloxy)ethyl]-phenyl}2H-benzotriazole;

(e) 5-trifluoromethyl-2-{2-hydroxy-3-α-cumyl-5-[2-(3-triethyoxysilyl)propylcarbamoyl-oxy)ethyl]phenyl}-2H-benzotriazole;

(f) 5-trifluoromethyl-2-{2-hydroxy-3-tert-butyl-5-[2-(3-(diethoxymethylsilyl)propylamino-carbonylethyl]phenyl}2H-benzotriazole;

(g) 5-phenylsulfonyl-2-{2-hydroxy-3-tert-butyl-5-[3-(2-ethoxydimethylsilyl)ethylcarbonyl-oxy)propyl]phenyl}2H-benzotriazole;

(h) 5-n-butylsulfonyl-2-{2-hydroxy-3-tert-butyl-5-[2-(3-ethoxydimethylsilyl)propyl-oxycarbonyl)ethyl]phenyl}2H-benzotriazole;

(i) 5-trifluoromethyl-2-[2-hydroxy-3-(ethoxydimethylsilyl)propyl-5-tert-octylphenyl]-2H-benzotriazole;

(j) 5-trifluoromethyl-2-[2-hydroxy-3-(trimethylsilyl)propyl-5-tert-butylphenyl]-2H-benzotriazole;

(k) 5-[3-(diethoxyethylsilyl)propoxycarbonyl]-2-(2-hydroxy-3-α-cumyl-5-tert-octyl-phenyl)-2H-benzotriazole;

(l) 5-[3-(diethoxyethylsilyl)propylaminocarbonyl]-2-(2-hydroxy-3-α-cumyl-5-tert-octyl-phenyl)-2H-benzotriazole;

(m)
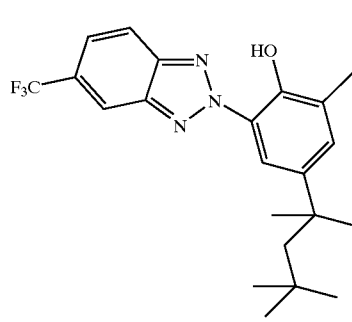

(n)
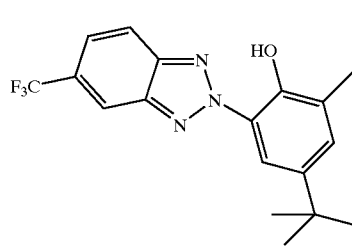

(o)
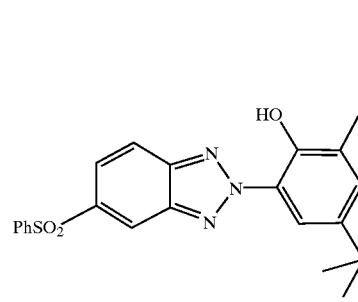

(p)
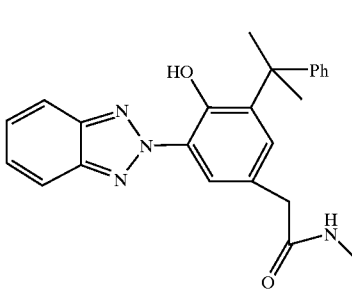

-continued (q)
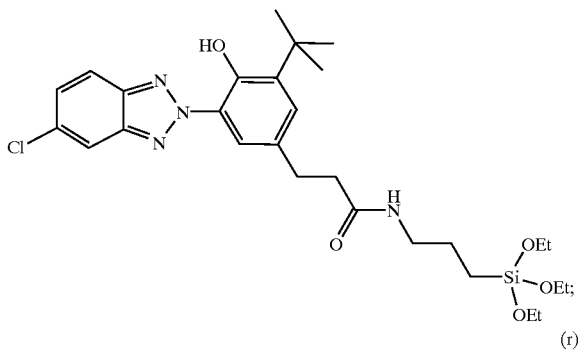

(r)
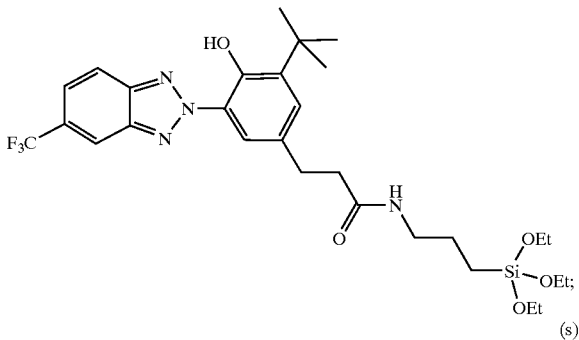

(s)
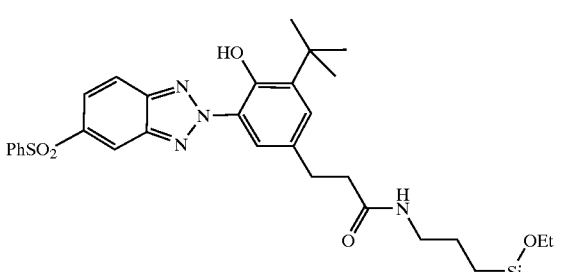

(t)
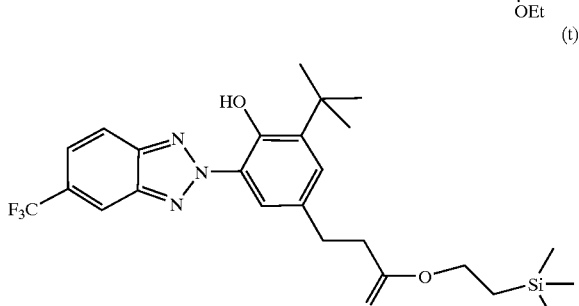

or (u)
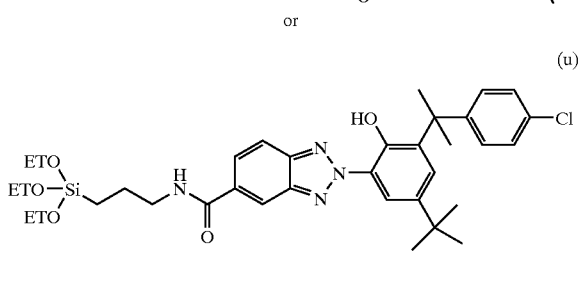

* * * * *